United States Patent
Kiwa et al.

(10) Patent No.: US 8,710,440 B2
(45) Date of Patent: Apr. 29, 2014

(54) MEASURING DEVICE AND MEASURING METHOD THAT USE PULSED ELECTROMAGNETIC WAVE

(75) Inventors: Toshihiko Kiwa, Okayama (JP); Keiji Tsukada, Okayama (JP)

(73) Assignee: National University Corporation Okayama University, Okayama-shi, Okayama (JP)

( * ) Notice: Subject to any disclaimer, the term of this patent is extended or adjusted under 35 U.S.C. 154(b) by 0 days.

(21) Appl. No.: 13/577,604

(22) PCT Filed: Feb. 7, 2011

(86) PCT No.: PCT/JP2011/052529
§ 371 (c)(1),
(2), (4) Date: Aug. 7, 2012

(87) PCT Pub. No.: WO2011/096563
PCT Pub. Date: Aug. 11, 2011

(65) Prior Publication Data
US 2012/0305774 A1    Dec. 6, 2012

(30) Foreign Application Priority Data

Feb. 8, 2010    (JP) ................................. 2010-025991

(51) Int. Cl.
| | | |
|---|---|---|
| *G01J 5/10* | (2006.01) | |
| *G01J 5/02* | (2006.01) | |
| *G01T 1/24* | (2006.01) | |
| *G01N 21/35* | (2014.01) | |
| *A61B 5/05* | (2006.01) | |

(52) U.S. Cl.
CPC .............. *G01T 1/24* (2013.01); *G01N 21/3581* (2013.01); *A61B 5/05* (2013.01)
USPC ........................................ 250/330; 250/341.1

(58) Field of Classification Search
CPC .... G01T 1/24; G01T 1/2928; G01N 21/3581; A61B 5/05
USPC ............................................... 250/341.1, 330
See application file for complete search history.

(56) References Cited

U.S. PATENT DOCUMENTS

| | | | |
|---|---|---|---|
| 7,681,434 B2 | 3/2010 | Ouchi | |
| 2007/0145276 A1* | 6/2007 | Zhang et al. | 250/341.1 |
| 2007/0158571 A1* | 7/2007 | Cole et al. | 250/341.8 |
| 2010/0220327 A1 | 9/2010 | Kiwa et al. | |

FOREIGN PATENT DOCUMENTS

| | | |
|---|---|---|
| JP | 2004-198250 | 7/2004 |
| JP | 2007-064700 | 3/2007 |
| JP | 2007-078621 | 3/2007 |
| JP | 2008-170353 | 7/2008 |
| JP | 2008-277565 | 11/2008 |
| JP | 4183735 | 11/2008 |
| JP | 2009-097933 A * | 7/2009 |

OTHER PUBLICATIONS

International Search Report for International Application No. PCT/JP2011/052529, Japanese Patent Office, mailed Mar. 22, 2011, 4 pgs.

\* cited by examiner

*Primary Examiner* — David Porta
*Assistant Examiner* — Abra Fein
(74) *Attorney, Agent, or Firm* — Sterne, Kessler, Goldstein & Fox P.L.L.C.

(57) ABSTRACT

Provided are a measuring device and a measuring method that use terahertz light, by which a substance to be detected can be detected with high sensitivity and high accuracy. A measuring device using a pulsed electromagnetic wave is provided with a substance detection plate, a means for generating the pulsed electromagnetic wave having amplitude intensity dependent on the amount of a substance to be detected at an irradiation position by irradiating the substance detection plate with a pulsed laser beam, and a detection means for detecting the amplitude intensity of the pulsed electromagnetic wave, and measures the change of the state of a solution containing the substance to be detected on the basis of the amplitude intensity.

6 Claims, 17 Drawing Sheets

MEASURING DEVICE AND MEASURING METHOD THAT USE PULSED ELECTROMAGNETIC WAVE

BACKGROUND OF THE INVENTION

1. Technical Field

The present invention relates to a measuring device and a measuring method that use a pulsed electromagnetic wave. Particularly, the present invention relates to a measuring device and a measuring method that perform measurement by detecting a time change in the electric field strength of a pulsed electromagnetic wave.

2. Background Art

Electromagnetic waves that have a frequency of 10 GHz to 10 THz or include components in a wide frequency domain (called terahertz band) including further the frequency domain are collectively called terahertz beam. In particular, spectral devices and imaging devices have been proposed for a time domain in which terahertz pulsed beams (called pulsed terahertz pulsed beam) are used.

These devices are configured to radiate terahertz pulsed beams onto various measurement object samples, such as semiconductors and dielectrics, so that the beams transmit through or are reflected on the measurement object samples. Then, a time change of the electric field strength of the pulsed beams is detected. Thus, electric field strength and phase information in each frequency is acquired by Fourier transform. As a result, it becomes possible to acquire in a non-destructive manner the physicality data of each of the various measurement object samples that cannot be acquired or have been difficult to acquire by a Fourier spectrum device.

In order to acquire information on a sample by use of the terahertz pulsed beams, in addition to a time-domain wave from the samples, a reference time-domain wave is needed. As a reference waveform, in the case of a transmission type, a wave detected without a sample is used. In the case of a reflection type, a wave detected with a mirror deemed to have a reflection ratio of 100% is disposed in place of a sample, is used as a reference waveform. The resultant reference waveform is also subjected to the Fourier transform so as to acquire the amplitude intensity and phase information of an electric field for each wavelength.

Patent document 1 discloses a measuring method that uses a terahertz pulsed beam in a case where a sample is limited to a parallel flat plate. The measuring method uses as a reference signal a reflected pulsed beam that is reflected from an incidence surface of the sample and included in a time-domain wave of the reflected beam. Then, the reflected pulsed beam is detected from the time-domain wave of the reflected beam. The measurement is conducted with a differential signal, as a sample signal, acquired by removing the reflected pulsed beam from the time-domain wave of the reflected beam.

RELATED ART DOCUMENTS

Patent Documents

Patent Document 1: Japanese Unexamined Patent Application Publication No. 2004-198250.
Patent Document 2: Japanese Patent No. 4183735.

DISCLOSURE OF THE INVENTION

Problems to be Solved by the Invention

Unfortunately, in the conventional devices that use a terahertz pulsed beam, detection sensitivity and detection accuracy are not sufficient. For example, in a measuring device that uses a pulsed electromagnetic wave described in patent document 2, further improvement of detection sensitivity and detection accuracy are called for the application to the field of drug development.

Accordingly, an object of the present invention is to provide a measuring device and a measuring method that use pulsed electromagnetic waves and can detect a detection object substance with high sensitivity and high precision.

Means of Solving the Problems

The problems to be solved by the invention are as described above. Next, means for solving the problems will be described.

Specifically, in claim 1, a measuring device that uses a pulsed electromagnetic wave, includes:
  a substance detecting plate including a semiconductor and an insulator formed on the semiconductor;
  a means configured to radiate a pulsed laser beam onto the substance detecting plate from a side of the semiconductor to generate a pulsed electromagnetic wave with an amplitude intensity depending on an amount of a detection object substance at an irradiated position; and
  a detecting means configured to detect the amplitude intensity of the pulsed electromagnetic wave,
  in which the measuring device is configured to measure a change in a state of a solution containing the detection object substance from the amplitude intensity, the measuring device further includes:
    a first beam splitter configured to split the pulsed laser beam into two beams;
    a detected region that is disposed on the insulator and into which a solution containing a detection object substance is able to be introduced; and
    a reference region that is disposed in a vicinity of the detected region on the insulator and into which a reference solution is able to be introduced, and
  in which the pulsed laser beam is split into two split pulsed laser beams by the first beam splitter; one split pulsed laser beam of the two split pulsed laser beams is radiated onto the semiconductor corresponding to the detected region; the other split pulsed laser beam is radiated onto the semiconductor corresponding to the reference region; pulsed electromagnetic waves generated from the semiconductor corresponding to the detected region and the reference region are focused by a focusing means to be detected by the detecting means that is provided in singular.

In claim 2, the measuring device that uses the pulsed electromagnetic wave further includes:
  a second beam splitter configured to split the pulsed laser beam into two beams of a probe beam and a pump beam; and
  a time delaying means disposed on an optical path of the probe beam and capable of delaying a time at which the amplitude intensity is detected by the detecting means,
  in which the pump beam is split into two split pump beams by the first beam splitter; one split pump beam of the two split pump beams is radiated onto the semiconductor corresponding to the detected region; the other split pump beam is radiated onto the semiconductor corresponding to the reference region; pulsed electromagnetic waves generated from the semiconductor corresponding to the detected region and the reference region are focused by the focusing means to be incident on the detecting means provided in singular, in which the probe beam passes through the time delaying means to be radiated onto the detecting means in synchronization with a timing at which the pulsed electromagnetic waves generated by the respective pump beams are made incident, and in which the amplitude intensity of each of the pulsed electromagnetic waves that are generated by the respective pump beams and made incident on the detecting means at a timing at which the probe beam is radiated, is detected.

In claim 3, in the measuring device that uses the pulsed electromagnetic wave, the time delaying means is able to periodically delay the timing at which the amplitude intensity is detected by the detecting means.

In claim 4, the measuring device that uses the pulsed electromagnetic wave further includes:

a second beam splitter configured to split the pulsed laser beam into two beams of a probe beam and a pump beam; and a pulse timing adjusting means disposed on an optical path of the pump beam between the first beam splitter and the semiconductor and capable of adjusting a pulse timing of the pump beam as desired, in which the pump beam is split into two split pump beams by the first beam splitter; one split pump beam of the two split pump beams is radiated onto the semiconductor corresponding to the detected region; the other split pump beam is radiated onto the semiconductor corresponding to the reference region; either one of the one split pump beam and the other split pump beam passes through the pulse timing adjusting means; pulsed electromagnetic waves generated from the semiconductor corresponding to the detected region and the reference region are focused by the focusing means to be incident on the detecting means provided in singular, in which the pulse timing adjusting means is configured to preliminarily adjust the pulse timing of one of the one split pump beam and the other split pump beam so that detection timings of the respective amplitude intensities of the pulsed electromagnetic waves detected by the detecting means match, in which the probe beam is radiated onto the detecting means in synchronization with a timing at which the pulsed electromagnetic waves generated by the respective pump beams are made incident, and in which the amplitude intensity of each of the pulsed electromagnetic waves that are generated by the respective pump beams and made incident on the detecting means at a timing at which the probe beam is radiated, is detected.

In claim 5, a measuring method that uses a pulsed electromagnetic wave and uses:

a substance detecting plate including a semiconductor and an insulator formed on the semiconductor;

a means configured to radiate a pulsed laser beam onto the substance detecting plate from a side of the semiconductor to generate a pulsed electromagnetic wave with an amplitude intensity depending on an amount of a detection object substance at an irradiated position; and a detecting means configured to detect the amplitude intensity of the pulsed electromagnetic wave, to measure a change in a state of a solution containing the detection object substance from the amplitude intensity, the measuring method including:

a splitting step of splitting the pulsed laser beam into two beams of a probe beam and a pump beam;

an incidence step of splitting the pump beam into two split pump beams, radiating, one split pump beam of the two split pump beams onto the semiconductor corresponding to a detected region into which a solution containing the detection object substance is able to be introduced, radiating the other split pump beam onto the semiconductor corresponding to a reference region into which a reference solution is able to be introduced, focusing pulsed electromagnetic waves generated from the semiconductor corresponding to the detected region and the reference region so that the pulsed electromagnetic waves are made incident on the detecting means provided in singular;

a step of radiating the probe beam onto the detecting means in synchronization with a timing at which the pulsed electromagnetic waves generated by the respective pump beams are made incident, the probe beam being subjected to time delay at a predetermined cycle;

a time-domain waveform generating step of detecting the amplitude intensity of each of the pulsed electromagnetic waves that are generated by the respective pump beams and made incident on the detecting means at a timing at which the probe beam is radiated, thereby acquiring the amplitude intensity of each of a plurality of the pulsed electromagnetic waves respectively in the detected region and the reference region and being different in delay time, and producing a time-domain waveform of the pulsed electromagnetic waves respectively in the detected region and the reference region;

an amplitude acquisition step of acquiring an amplitude intensity at each wave peak position from the time-domain waveform of the pulsed electromagnetic waves produced by the time-domain waveform generating step in each of the detected region and the reference region; and a differentiation step of differentiating the amplitude intensities respectively at the wave peak position in the detected region and the wave peak position in the reference region.

In claim 6, a measuring method that uses a pulsed electromagnetic wave uses:

a substance detecting plate including a semiconductor and an insulator formed on the semiconductor;

a means configured to radiate a pulsed laser beam onto the substance detecting plate from a side of the semiconductor to generate a pulsed electromagnetic wave with an amplitude intensity depending on an amount of a detection object substance at an irradiated position; and a detecting means configured to detect the amplitude intensity of the pulsed electromagnetic wave, to measure a change in a state of a solution containing the detection object substance from the amplitude intensity, the measuring method including:

a splitting step of splitting the pulsed laser beam into two beams of a probe beam and a pump beam;

an incidence step of splitting the pump beam into two split pump beams, radiating one split pump beam of the two split pump beams onto the semiconductor corresponding to a detected region into which a solution containing the detection object substance is able to be introduced, radiating the other split pump beam onto the semiconductor corresponding to a reference region into which a reference solution is able to be introduced, focusing pulsed electromagnetic waves generated from the semiconductor corresponding to the detected region and the reference region so that the pulsed electromagnetic waves are made incident on the detecting means provided in singular;

a pulse arrival timing adjusting step of preliminary adjusting a pulse timing of one of the one split pump beam and the other split pump beam such that detection timings of the respective amplitude intensities of the pulsed electromagnetic waves detected by the detecting means match;

a step of radiating the probe beam onto the detecting means in synchronization with a timing at which the pulsed electromagnetic waves generated by the respective pump beams are made incident; and a step of detecting the amplitude intensity of each of the pulsed electromagnetic waves that are generated by the respective pump beams and made incident on the detecting means at a timing at which the probe beam is radiated.

Effect of the Invention

According to the present invention, the detection sensitivity and the detection accuracy of a measuring device can be improved.

Figure 1:
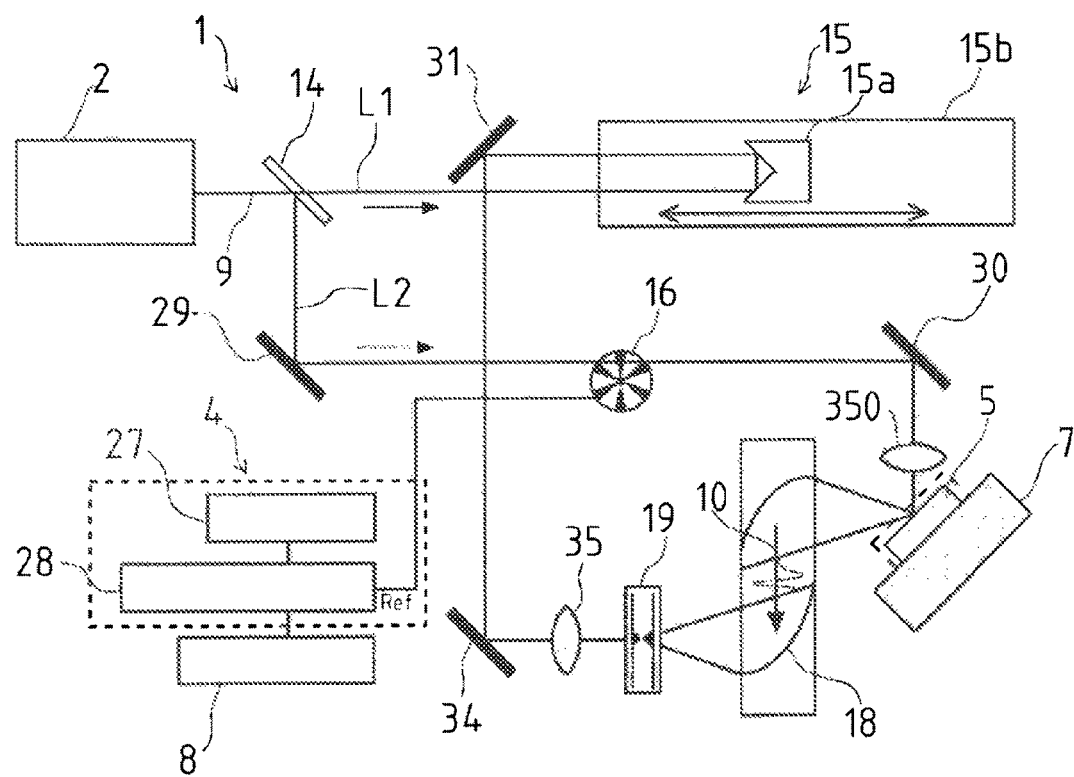
FIG. 1 is a schematic diagram of a measuring device that uses a pulsed electromagnetic wave according to the present invention.

DESCRIPTION OF REFERENCE NUMERAL 1, 50 measuring device
2 pulsed laser beam source
4 detecting and converting device
5 substance detecting plate
9 pulsed laser beam
10 pulsed electromagnetic wave
12 flow path (detected region)
13 reference region
14 second beam splitter
15 time delaying means
17 first beam splitter
18, 40 focusing means
22 insulator
23 semiconductor

MODE FOR CARRYING OUT THE INVENTION

Hereafter, description will be given on the best mode of the present invention with reference to drawings. Each of parts common among the drawings is indicated by the same reference sign, and duplicated description thereof is omitted.

FIG. 1 shows a first embodiment of a measuring device that uses pulsed electromagnetic waves according to the present invention.

A solution concentration distribution measuring device 1 (hereafter, referred to as a measuring device 1) is a measuring device that uses pulsed electromagnetic waves 10, and includes a substance detecting plate 5 (sensing plate), a flow path 12, a reference region 13 (refer to FIG. 7), a stabilizing means (below-mentioned reference electrode 26), a generating means (pulsed laser beam source 2), a second beam splitter 14, a radiating means (scanning table 7, pulsed laser beam source 2), a measuring means (detecting and converting device 4), a time delaying means 15, and an acquiring means (controlling and analyzing device 8). The substance detecting plate 5 includes a semiconductor 23, an insulator 22 formed on the semiconductor 23, and a substance sensitive film 21 formed on the insulator 22. The flow path 12 is disposed on the insulator 22 (substance sensitive film 21), a solution containing a detection object substance flows therethrough, and serves as a detecting region in which the solution containing a detection object substance can be introduced. The reference region 13 is disposed in the vicinity of the flow path 12 on the insulator 22 (substance sensitive film 21), and a reference solution can be introduced therethrough. The stabilizing means (reference electrode 26) is configured to stabilize the electric potential of a solution. The generating means (pulsed laser beam source 2) is configured to radiate a pulsed laser beam 9 onto a position corresponding to the flow path on the substance detecting plate 5 from the semiconductor 23 side being an opposite side of the insulator 22, thereby generating the pulsed electromagnetic wave 10 having an amplitude intensity depending on an amount of the detection object substance at the irradiated position. The second beam splitter 14 is configured to split the pulsed laser beam 9 radiated from the pulsed laser beam source 2 into two beams of a probe beam L1 and a pump beam L2. The radiating means (scanning table 7, pulsed laser beam source 2) is configured to radiate the pulsed laser beam 9 in a two-dimensional scanning manner The measuring means (detecting and converting device 4) is configured to measure the amplitude intensity of the pulsed electromagnetic wave 10. The time delaying means 15 is disposed on the optical path of the probe beam L1, and configured to be able to delay periodically the time to detect the amplitude intensity by the detecting and converting device 4. The acquiring means (controlling and analyzing device 8) is configured to measure the detection object substance qualitatively or quantitatively from the amplitude intensity, thereby acquiring the reaction distribution or concentration distribution of the substance in the solution in the flow path 12. Further, in this embodiment, a substance sensitive film 21 mentioned below constitutes a part (in this embodiment, a bottom portion of the inner wall surface of the flow path 12) of the inner wall surface of the flow path 12 in a flow-path forming portion 6. Hereafter, a principle relating to the present invention and the details of a device constitution will be described.

In the above description, the controlling and analyzing device 8 is not particularly limited to the acquiring means for acquiring the reaction distribution or concentration distribution of a substance in a solution, and may be a means for measuring the characteristics of a solution containing the detection object substance, a change of the characteristics, and a change in the state of a solution.

Further, in this embodiment, a portion located at the substance detecting plate 5 side on an inner wall surface of the flow path 12 is called a bottom portion for convenience sake.

First, description will be given to the principle of generation of electromagnetic wave by laser pulse radiation. When a position on the semiconductor at which an electric field E exists is irradiated with a laser beam having larger energy than a band gap, electron-hole pairs are generated by photoexcitation. Successively, the electron-hole pairs are accelerated by the electric field E, thereby generating an electric current. In the case where the laser beam is a continuous beam, the current flows constantly. However, in the case where the laser beam is a pulsed beam, the excited electron-hole pairs are relaxed after certain given time and the electric current stops flowing. Accordingly, a pulsed electric current flows in accordance with the width and relaxation time of a beam pulse. According to the following Formula (1) led from the Maxwell equation of the classic electromagnetics, when temporal change occurs in an electric current flowing in a semiconductor, an electromagnetic wave is emitted from the semiconductor.

[Mathematical Formula 1]

$$\vec{E}_{emission} \propto \frac{\partial \vec{J}}{\partial t} = \frac{\partial (ne\vec{v})}{\partial t} = \frac{\partial (ne\mu\vec{E}_{local})}{\partial t} \quad (1)$$

In Formula (1), $E_{emission}$ represents an electric field vector of an electromagnetic wave, J represents a photocurrent density vector, n represents the density of photoexcited electron-hole pairs, e represents an elementary charge amount, v represents the drift velocity of the electron-hole pair accelerated by an electric field $E_{local}$ in the semiconductor at the position irradiated with a beam, and μ represents the mobility of electric charge.

As can be understood from Formula (1), the amplitude strength of the generated electromagnetic wave is proportional to the electric field $E_{local}$ in the semiconductor at the beam irradiated position.

Next, reason will be described why the amplitude strength of the pulsed electromagnetic wave 10 generated from the semiconductor 23 by the radiation of the pulsed laser beam 9 changes in the case where a detection object substance in a solution exists on the surface of the substance detecting plate 5 formed on the semiconductor 23.

First, when a solution including a detection object substance comes in contact with a substance sensitive film sensing a specific detection object substance, the concentration of hydrogen ions in the solution changes. Specifically, pH of the solution being in contact with the substance sensitive film changes.

For example, it is known that in the substance sensitive film including urease (enzyme), urea is hydrolyzed by a catalyst action, thereby generating ammonia, which results in the rise in pH.

Figure 2:
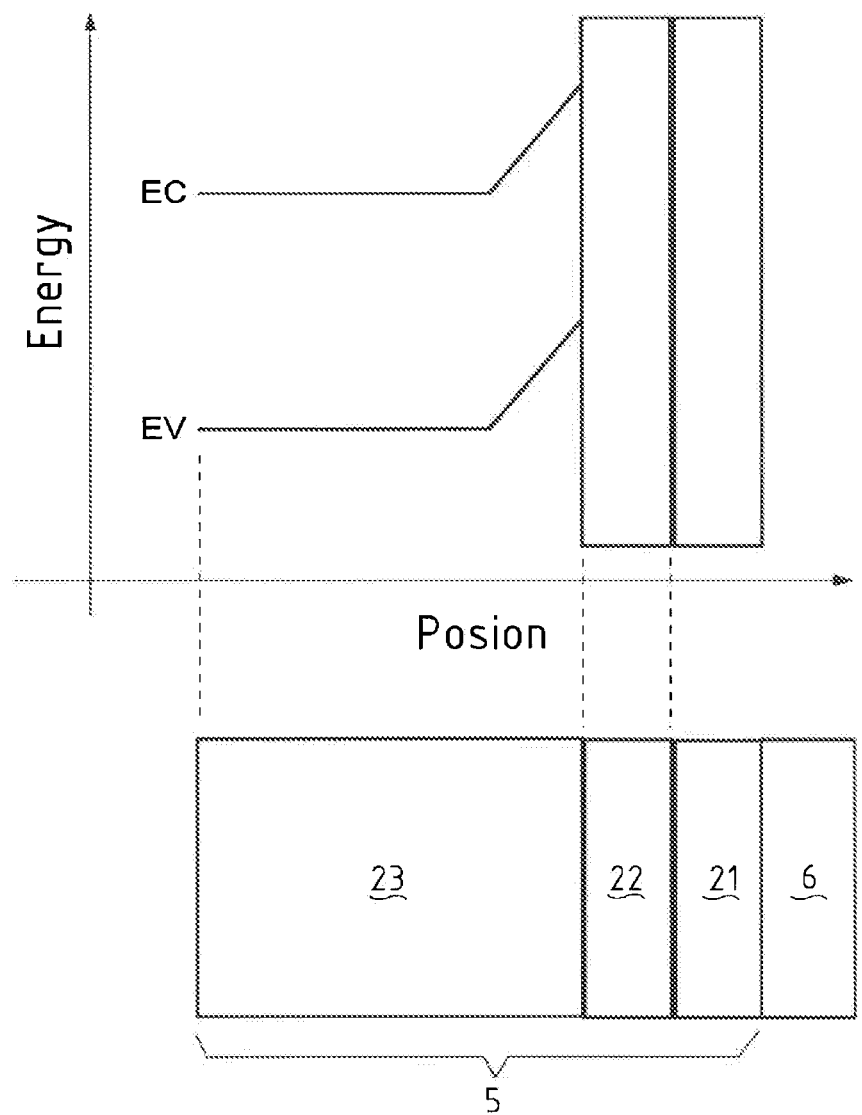
FIG. 2 is a schematic diagram of an energy band distribution of a substance detecting plate according to the present invention.

FIG. 2 is a schematic diagram of an energy band distribution of a substance detecting plate. The horizontal axis indicates position, and the vertical axis indicates energy. In the drawing, EC represents a conduction band, and EV represents a valence band. At the boundary between the insulator 22 and the semiconductor 23, a depletion layer is formed. The depletion layer is a region with no carrier, and in the depletion layer, a local electric field E is formed. Accordingly, an electric field constantly exists in the depletion layer even when no voltage is applied from the outside. When this depletion layer is irradiated with a beam so as to generate electron-hole pairs, an electromagnetic wave is generated in accordance with Formula (1).

The orientation and magnitude of the local electric field E may change depending on the state of the boundary between the insulator 22 and the semiconductor 23 and the characteristics of the semiconductor 23. However, an especially-important point in the principle of generation of an electromagnetic wave resides in the fact that the local electric field E is formed.

As shown in FIG. 2, a change in the concentration of hydrogen ions in the solution (pH of the solution) causes a change in the density of each of hydrogen ions and hydroxyl ions both adsorbed by the substance sensitive film 21, which leads to the change in the electric charge on the surface of the substance sensitive film 21. The change of the electric charge causes a change in the local electric field E in the depletion layer formed at the boundary between the insulator 22 and the semiconductor 23. As a result, the amplitude strength of the electromagnetic wave proportional to the local electric charge E also changes.

As mentioned above, the direct measurement of the amplitude strength of the electromagnetic wave generated by the radiation of the pulsed laser beam 9 enables detection of a detection object substance without fabrication of an electrode to read out a signal for each detection object substance.

On the basis of the above principle, a detection object substance is detected by the device constitution of the measuring device 1 shown in FIG. 1 according to the first embodiment.

FIG. 1 is a schematic drawing of the solution concentration distribution measuring device of this embodiment. As shown in this drawing, the solution concentration distribution measuring device 1 of this embodiment includes a radiating device (optical system), the detecting and converting device 4 and the controlling and analyzing device 8.

In FIG. 1, the radiating device (optical system) mainly includes the pulsed laser beam source 2, the second beam splitter 14, the time delaying means 15, a light beam chopper 16, a pump beam splitting and focusing means (a first beam splitter 17 (refer to FIG. 7), a focusing means 18), and a scanning table 7. The radiating device (optical system) has a function to radiate the pulsed laser beam 9 (pump beam L2) having a predetermined wavelength to the flow path 12 that is disposed at a predetermined position on the substance detecting plate 5 and serves as the detected region and to the reference region 13.

In this regard, the constitution of mirrors and the like used for changing the direction of the pulsed laser beam 9 is not limited to that in this embodiment, and the constitution may be changed appropriately, for example, the number of mirrors may be increased, in consideration of the arrangement of each of the constitutional components.

Furthermore, the radiating device includes the scanning means for radiating the pulsed laser beam 9 in a two-dimensional scanning manner. Specifically, the scanning means has a function to radiate the pulsed laser beam 9 to the substance detecting plate 5 on the scanning table 7 while causing the substance detecting plate 5 and the flow path forming portion 6 reciprocate on the scanning table 7 (XY automatic stage) by a driving device (not shown).

Figure 4:
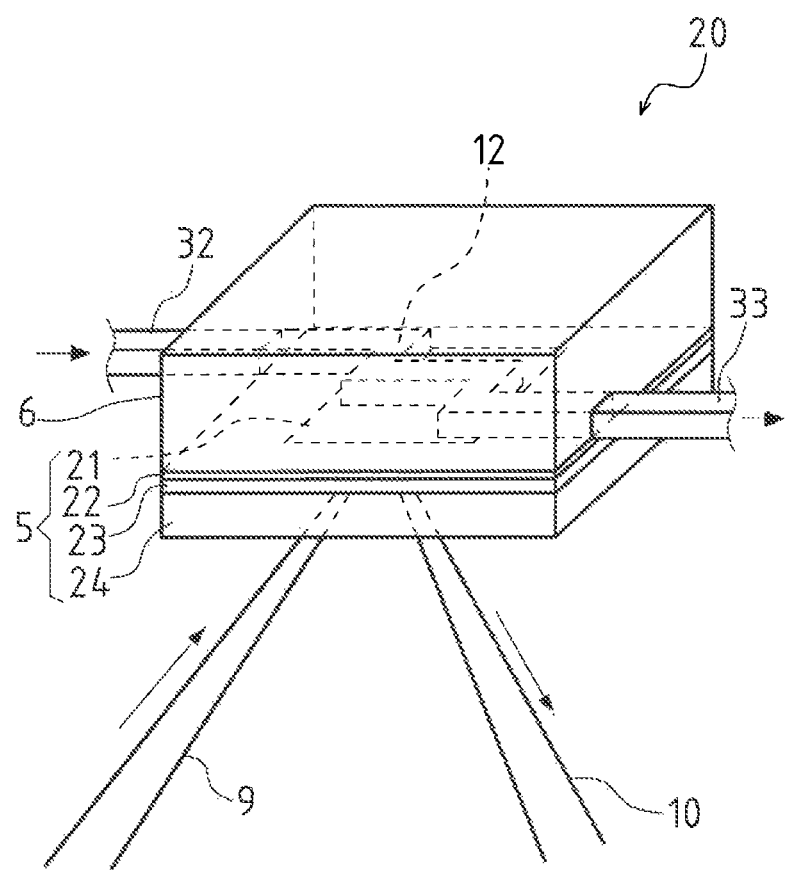
FIG. 4 is a perspective view showing a flow path forming portion and a flow path.

As shown in FIG. 4, the pump beam L2 being a split light beam of the pulsed laser beam 9 is radiated onto the semiconductor 23 at the position corresponding to the substance sensitive film 21 constituting the bottom portion of the flow path 12 (radiated onto the flow path 12 located at one side surface portion of the flow path forming portion 6). The whole body of the substance detecting plate 5 and the flow path forming portion 6 laminated in a close contact state on the substance detecting plate 5 is moved on the scanning table 7 so that the semiconductor 23 corresponding to the substance sensitive film 21 on the bottom of the flow path 12 is moved to a position irradiated with the pump beam L2, whereby the laser beam irradiated surface of the semiconductor 23 is scanned with the pump beam L2. By radiating the pump beam L2, a pulsed electromagnetic wave 10 is generated continuously from the laser beam-irradiated position of the semiconductor 23.

The scanning constitution is not be limited to the constitution in this first embodiment. For example, the pulsed laser beam 9 may be made to scan two-dimensionally on the substance detecting plate 5 by a mirror (not shown) being oscillated or rotated or by radiation from the pulsed laser beam source 2 being oscillated.

As shown in FIG. 1, in this embodiment, the plane formed by the paths of the pulsed laser beam 9 and the pulsed electromagnetic wave 10 is an approximately horizontal plane. Specifically, FIG. 1 shows a constitution of a top view, and in the side view of this constitution, the pulsed laser beam 9 and the pulsed electromagnetic wave 10 are arranged to form an approximately horizontal plane. However, it is desirable to arrange them appropriately in accordance with the configuration and securing method of each device. Accordingly, it is not necessary to constitute such an approximately horizontal plane. Further, in this embodiment, the pump beam L2 split from the pulsed laser beam 9 is radiated onto the semiconductor 23 corresponding to one side of the flow path 12 (in this embodiment, the bottom side of the flow path 12) of the flow path forming portion 6.

The incident angle of the pump beam L2 being a split light beam of the pulsed laser beam 9 on the substance detecting plate 5 is preferably an angle at which the wavelength of the pulsed laser beam 9 is most absorbed by the semiconductor 23 of the substance detecting plate 5. However, depending on the configuration and securing method of each device, the incident angle is not necessarily limited to this angle, and is not particularly limited.

The pulsed laser beam source 2 is preferably a mode-locked titanium sapphire laser or a femtosecond fiber laser each of which can generate the pulsed laser beam 9.

Preferably, the pulsed laser beam 9 has a wavelength in a range of 300 nm (=0.3 μm) or more and 2 μm or less, a time-average energy of 0.1 mW or more and 10 W or less, and a pulse width of 1 femtosecond (1 fs=0.001 ps) or more and 10 picoseconds (10 ps) or less.

Specifically, at the time of excitation of an electromagnetic wave, by use of the pulsed laser beam 9 with a small duration as a light source, the electromagnetic wave can be excited without a largely affecting the semiconductor 23 and the solution. Further, specifically by use of a femtosecond laser beam as the pulsed laser beam 9, time resolution measurement can be achieved with high time resolution, whereby the reaction of a substance can be measured in real time. The maximum beam pulse width which does not provide a thermal influence to the semiconductor 23 and the solution can be estimated to be about 10 picoseconds. Furthermore, by use of the femtosecond laser beam, even if the solution of a minute amount, the influence of heating with a laser beam can be suppressed to the minimum. Accordingly, an effect that thermal destruction of a sample can be prevented is obtained.

The second beam splitter 14 is a means for splitting the pulsed laser beam 9 incident thereon into the probe beam L1 and the pump beam L2. In this embodiment, as the second beam splitter 14, a half mirror capable of splitting the pump beam L2 in the direction perpendicular to the probe beam L1 going straight ahead is employed.

The time delaying means 15 is disposed on the optical path of the probe beam L1, and is a means capable of delaying periodically the time at which the amplitude intensity is detected by the detecting and converting device 4. The time delaying means 15 includes a movable mirror 15*a* movable in a predetermined direction periodically by a driving means (not shown) and a stage 15*b* to hold the movable mirror 15*a*. The time delaying means 15 can reflect the probe beam L1 incident on the time delaying means 15 to a direction in parallel to and opposite to the entering direction of the probe beam L1. In this way, by making the movable mirror 15*a* reciprocate in parallel to the entering direction of the probe beam L1 periodically via the driving means, the time delaying means 15 adjusts the optical path length of the probe beam L1, thereby enabling to delay time optically. Further, the driving means is controlled by the controlling and analyzing device 8.

Specifically, by moving periodically the movable mirror 15*a* to adjust the optical path length of the probe beam L1, the time delaying means 15 can make the probe beam L1 provided with an amount of time delay of a predetermined time interval to be incident on the detecting and converting device 4 (a below-mentioned detecting element 19 included in the detecting and converting device 4).

The optical chopper 16 is disposed on the optical path of the pump beam L2, and can chop the pump beam L2 with a predetermined frequency.

Figure 7:
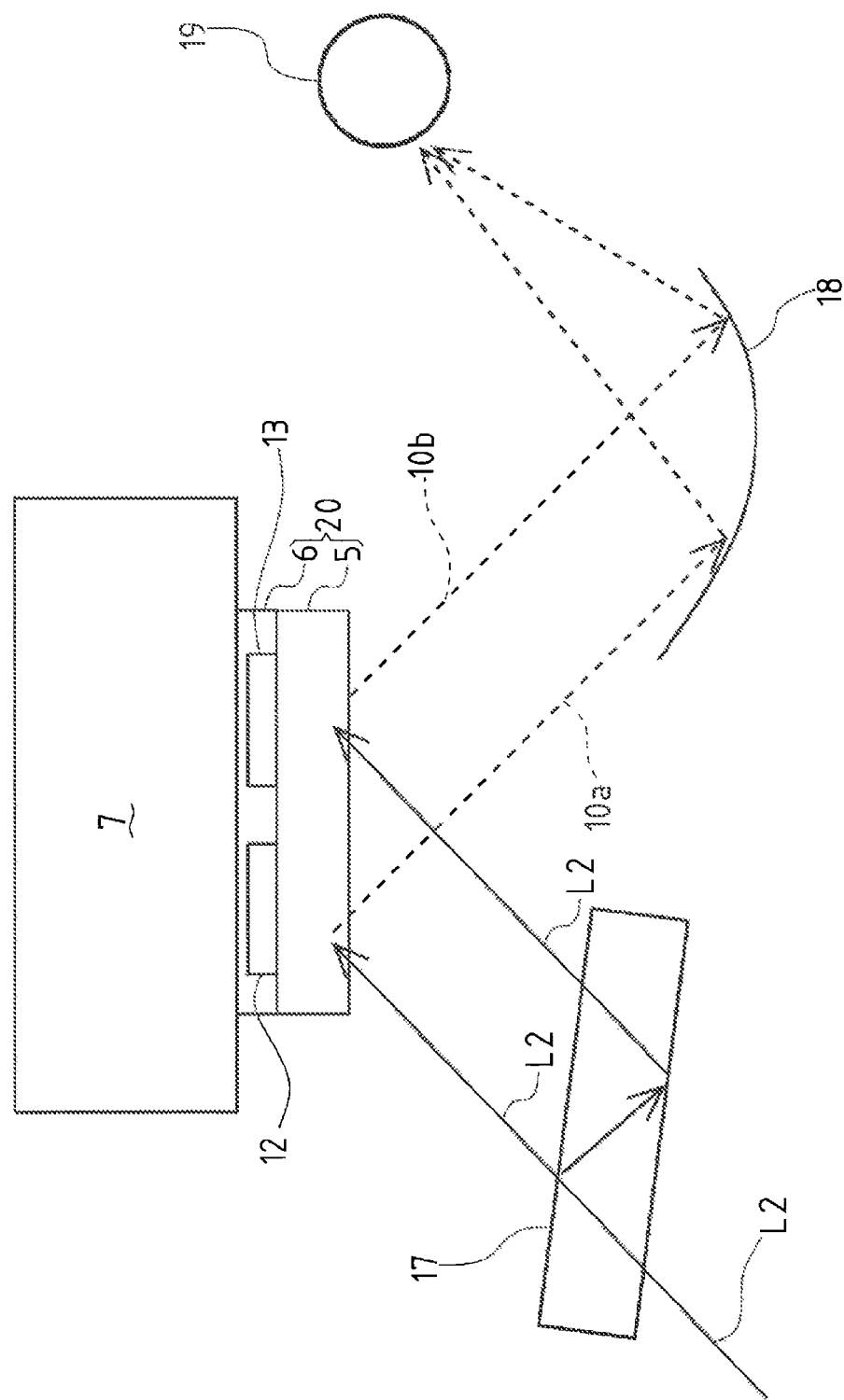
FIG. 7 is an illustration showing the substance detecting plate that includes a detected region and a reference region.

As shown in FIG. 7, the pump beam splitting and focusing means includes the first beam splitter 17 to split the entering pump beam L2 into two parallel pump beams L2 and an off-axis parabolic mirror serving as the focusing means 18 for focusing two pulsed electromagnetic waves 10*a* and 10*b* generated by the two parallel pump beams L2. This pump beam splitting and focusing means is configured to split the pump beam L2 being the pulsed laser beam 9 into two parallel pump beams L2 via the first beam splitter 17 (in the first embodiment, a flat plate for a beam splitter), to radiate one split pump beam L2 of the two parallel pump beams L2 onto the semiconductor 23 corresponding to the flow path 12 being a detected region, and to further radiate the other split pump beam L2 onto the semiconductor 23 corresponding to the reference region 13.

Figure 12:
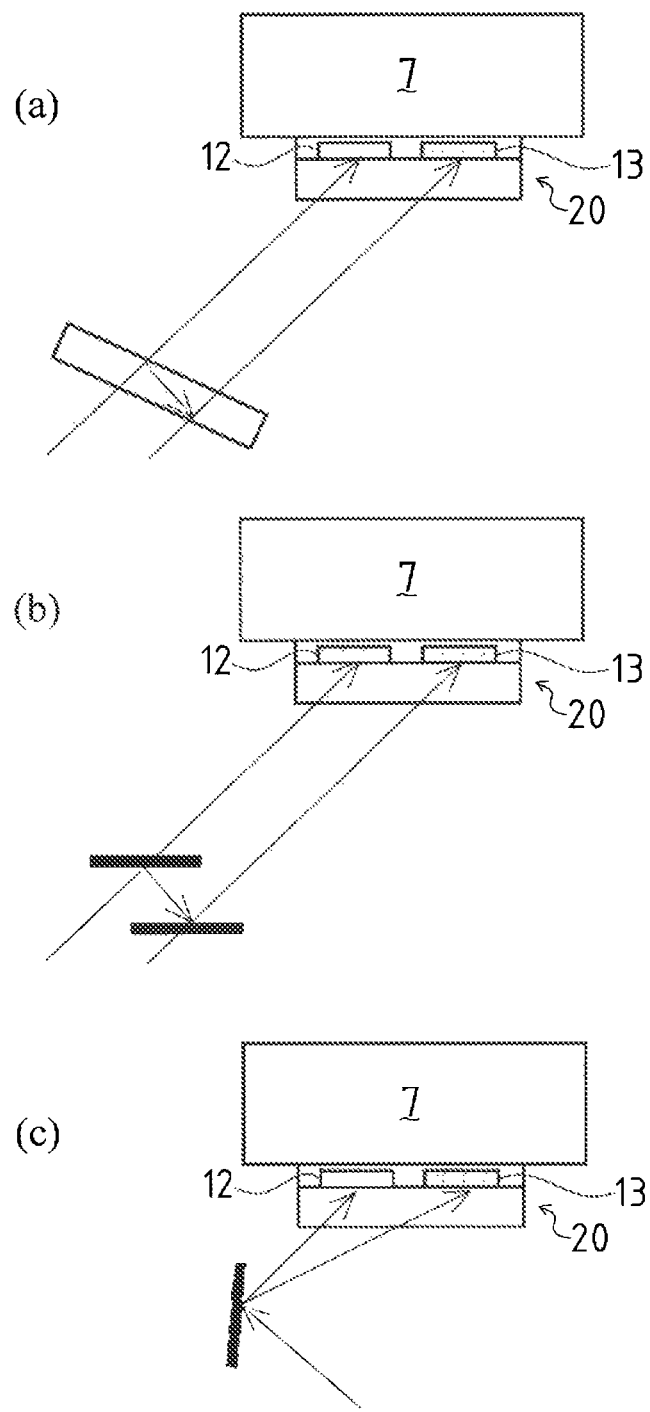
FIG. 12 is a schematic diagram showing examples of methods of splitting a laser beam, (a) is a schematic diagram showing a method of splitting a laser beam by inner reflection in a flat plate, (b) is a schematic diagram showing a method of splitting a laser beam by a half mirror and a mirror, and (c) is a schematic diagram showing a method of scanning with laser beams by a galvanometer mirror.

Examples of the first beam splitter 17 include, as shown in the laser beam splitting methods illustrated in FIG. 12, (a) a method of splitting via internal reflection in a flat plate by using the first beam splitter 17 serving as a flat plate for a beam splitter as in the first embodiment, (b) a method of splitting by using the half mirror 36 and the mirror 37 as in the below-mentioned second embodiment, and (c) a laser scan by a galvanometer mirror 38.

in FIG. 1, the detecting and converting device 4 includes the detecting element 19 serving as a detecting means and a converting means. The detecting and converting device 4 is configured to detect the pulsed electromagnetic waves 10*a* and 10*b* that are emitted from the respective positions irradiated with the pulsed laser beams 9 (pump beams L2) on the semiconductor 23 and focused by the off-axis parabolic mirror serving as the focusing means 18, and to convert them to respective voltage signals each of which changes in terms of time in response to the time wave of the electric field amplitude of the corresponding pulsed electromagnetic wave 10.

The detecting element 19 is a photoconductive antenna or the like for example, and the pulsed electromagnetic waves 10*a* and 10*b* can be irradiated thereon that are emitted from the respective positions irradiated with the pump beams L2 on the substance detecting plate 5. When the probe beam L1 is radiated onto a predetermined position on the detecting element 19 in synchronization with the incidence of one of the pulsed electromagnetic waves 10*a* and 10*b*, the detecting element 19 generates a current proportional to the electric field strength (amplitude intensity) of the one of the pulsed electromagnetic waves 10*a* and 10*b* made incident at the time of radiation of the probe beam L1.

The converting means includes a current amplifier 27 coupled to the detecting element 19 and a lock-in amplifier 28 coupled to the current amplifier 27. Further, the lock-in amplifier 28 is coupled to the optical chopper 16. This converting means can detect the amplitude intensity of one of the pulsed electromagnetic waves 10*a* and 10*b* made incident at the time of radiation of the probe beam L1 onto the detection element 19 by measuring the current generated by the detecting element 19. The frequency components included in the pulsed electromagnetic waves 10*a* and 10*b* are included within a range of from 10 GHz to 100 THz, whereby the detecting and converting device 4 with general constitutions can be utilized. Further, in the constitution of the solution concentration distribution measuring device according to the present invention, the pulsed electromagnetic wave 10 to be utilized is preferably in, a terahertz region than a gigahertz region. In the case of utilization of the terahertz region, unlike in the case of utilization of the gigahertz region, the electromagnetic wave can be guided easily to the detector with optical methods using mirrors, lenses, and the like. On the other hand, in the higher frequency region than the terahertz region, the electromagnetic wave becomes so-called light. In the case of utilization of light, there is a need to provide a means for discriminating the signal light from the surrounding light. As a result, the device becomes complicated. Accordingly, the electromagnetic wave in the terahertz region is used more preferably than electromagnetic waves with higher frequency than the terahertz region.

The controlling and analyzing device 8 is a device configured to perform detection of existence or absence of the detection object substance (qualitative measurement), quantitative measurement of the detection object substance, and measurement of reaction distribution and concentration distribution of the detection object substance from the voltage signals converted by the converting means of the detecting and converting device 4, and to further perform analytical processing such as predetermined analysis by use of the time-domain wave of the amplitude intensity (voltage value) of the pulsed electromagnetic wave 10 and predetermined calculation. Further, in this embodiment, the controlling and analyzing device 8 is a computer capable of executing the control and analysis described in this specification, and, in addition, is configured to control the radiating device (optical system), the scanning table 7, the detecting and converting device 4, and the pulsed laser beam source 2 via control signal lines (not shown).

Figure 3:
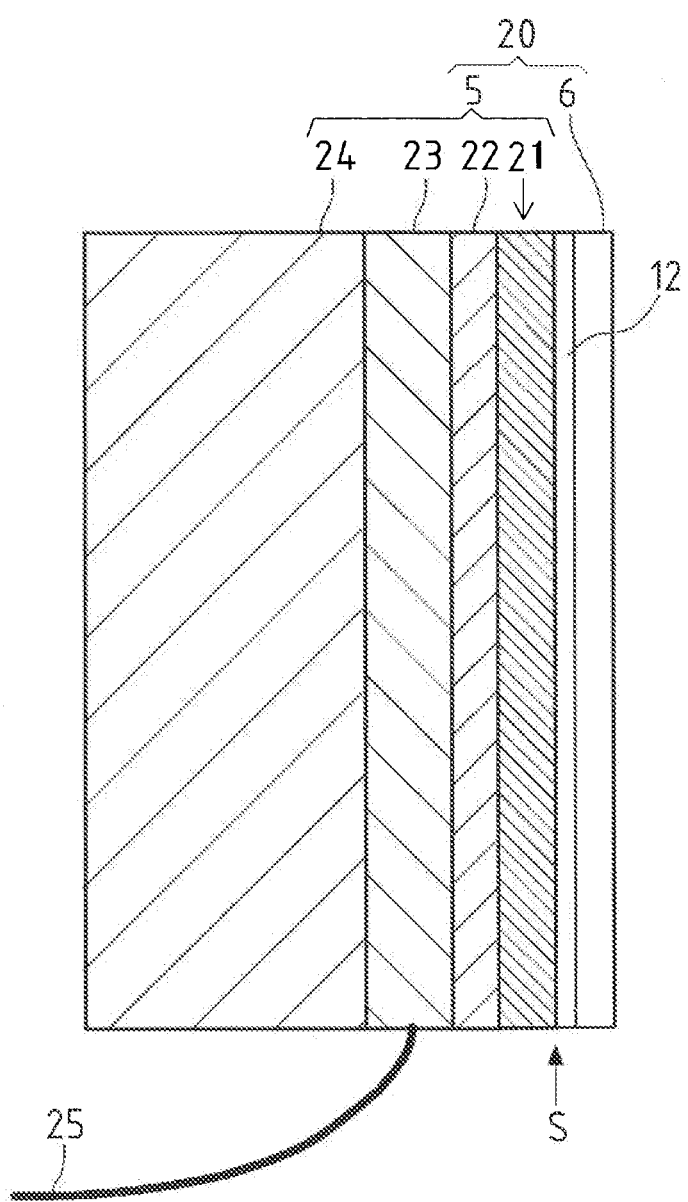
FIG. 3 is a schematic diagram of the substance detecting plate according to the present invention.

FIG. 3 is a schematic diagram of the substance detecting plate 5. The substance detecting plate 5 includes the substance sensitive film 21 that constitutes the bottom portion of the flow path 12 and the reference region 13, the insulator 22, the semiconductor 23, and a transparent substrate 24. Specifically, the substance detecting plate 5 includes the insulator 22; the semiconductor 23 that is formed so as to come in contact with one end surface (in FIG. 3, left end surface) of the insulator 22 and has a predetermined thickness; the transparent substrate 24 that is formed so as to come in contact with one end surface (in FIG. 3, left end surface) of the semiconductor 23; and the substance sensitive film 21 that is formed so as to come in contact with the other end surface (in FIG. 3, right end surface) of the insulator 22. Further, the substance detecting plate 5 and the flow path forming portion 6 constitute the measurement plate 20.

In the case of measurement of only pH of the solution, the substance sensitive film 21 is not needed.

Further, in the case where a film in which enzyme is immobilized is provided as the substance sensitive film 21 and a detection object substance that reacts with this enzyme exists in a solution, pH changes due to the reaction between the enzyme and the detection object substance, and the amplitude strength of the pulsed electromagnetic wave 10 generated at the position where the substance sensitive film 21 exists changes. By capturing this change of the amplitude strength, the detection object substance can be detected. Thus, the substance sensitive film 21 constituted with enzyme enables detection of distribution due to an enzyme reaction with the substance detecting plate 5. Specifically, the substance sensitive film 21 is constituted such that the enzyme is added to a light cross-linking agent and the resulting agent is coated on the bottom of the flow path 12. Alternatively, a sheet containing the enzyme is pasted on the bottom of the flow path 12.

Further, in the case where a film in which antigen is immobilized is provided as the substance sensitive film 21 and a detection object substance (antibody) that reacts with this antigen exists in a solution, electric charge on the surface of the substance sensitive film 21 changes due to the reaction between the antigen and the detection object substance (antibody), and the amplitude strength of the pulsed electromagnetic wave 10 generated at the position where the substance sensitive film 21 exists changes. From the value of this changed amplitude strength (relative to frequency), the detection object substance (antibody) can be detected. Thus, the substance sensitive film 21 constituted to include antigen enables detection of antibody corresponding to this antigen. As a result, the measuring device 1 can be utilized as a so-called biological sensor.

The size of the substance sensitive film 21 located at the bottom portion of the flow path 12 (a projected area of the semiconductor 23) is designed so as to correspond to the radiation range of the pulsed laser beam 9. Specifically, the size of the substance sensitive film 21 is designed to be larger than the irradiated range of the pulsed laser beam 9 (in this embodiment, the size of the substance sensitive film 21 is about 15 mm×15 mm, and the size of the substance sensitive film 21 shown in FIG. 6 corresponds to the measurement area). The size of the flow path 12 disposed on the substance sensitive film 21 in this embodiment is about 3 mm in the width of the flow path, about 2 mm in the height of the flow path, and about 18 mm in the length of the flow path (the length of flow path on the substance sensitive film 21). Specifically, the area of the substance sensitive film 21 constituting the inner wall surface of the flow path 12 is preferably not less than ¼ of the surface area of the inner wall of the flow path 12. The reason is that in the case where the area is less that ¼ of the surface area, an area to detect the reaction distribution might be insufficient. The width of the flow path 12 is preferably not more than ⅕ of the length of the flow path. The reason is that in the case where the width is larger than ⅕ of the length of the flow path, the thermal capacity becomes large so that sudden heating and cooling become difficult. Accordingly, the advantageous effect in conducting reaction by use of the micro flow path is not exerted.

As shown in FIG. 3, the film of the insulator 22 is formed on the semiconductor 23, and the substance sensitive film 21 is disposed on the insulator 22 and at a portion corresponding to the bottom portion of the flow path 12 and the reference region 13. In this embodiment, examples of the insulator 22 include silicon oxide, silicon nitride and the like. The thickness of the insulator 22 is about 270 nm, and the thickness of the semiconductor 23 is about 150 nm. However, in order to acquire large amplitude strength of the pulsed electromagnetic wave 10, it is preferable that the thickness of the semiconductor 23 is equal to a light penetration length determined based on the wavelength of the pulsed laser beam 9 and the type of the semiconductor 23. The light penetration length is the inverse number of an optical absorption coefficient of the semiconductor 23. For example, in the case where the wavelength of the pulsed laser beam 9 is 790 nm and the type of the semiconductor 23 is a silicon type with high resistance, the pulsed electromagnetic wave 10 can be efficiently generated when the thickness of the semiconductor 23 is about 2 micron.

As shown in FIG. 3, the transparent substrate 24 is needed at the time of producing the semiconductor 23, the insulator 22, and the substance sensitive film 21. Furthermore, the transparent substrate 24 is also needed to maintain mechanical strength of the substance detecting plate 5. In this embodiment, sapphire is used for the transparent substrate 24. Further, as shown in FIGS. 3 and 4, on the transparent substrate 24, the semiconductor 23 is disposed; on the semiconductor 23, the insulator 22 is disposed; and on the insulator 22, the substance sensitive film 21 is disposed.

As shown in FIG. 4, the pulsed laser beam 9 is radiated from the opposite side of the surface of the substance detecting plate 5 on which the substance sensitive film 21 is produced. In other words, the pulsed laser beam 9 (pump beam L2) is radiated onto the semiconductor 23 corresponding to the flow path 12, that is, onto the surface (in FIG. 4, the lower surface of the semiconductor 23) of the semiconductor 23 just below the flow path 12 in FIG. 4. Then, as the semiconductor provided on the substance detecting plate 5, one is used in which a semiconductor film (semiconductor 23) is formed on an insulator substrate (transparent substrate 24) through which the pulsed laser beam 9 is transmitted.

As shown in FIG. 3, a lead wire 25 is electrically coupled to the semiconductor 23 and thus a voltage can be applied on the semiconductor 23 as needed. With this, the width of a depletion layer in the semiconductor 23 can be controlled.

By producing a protective film made of silicon nitride or the like on the insulator 22, the situation can be avoided in which ions in the solution penetrate into the insulator 22 leading to unstable detection signals.

As shown in FIG. 7, the reference region 13 is disposed in the vicinity of the flow path 12 serving as the detected region on the substance sensitive film 21 disposed on the insulator 22, and reference solution can be introduced thereto.

Figure 5:
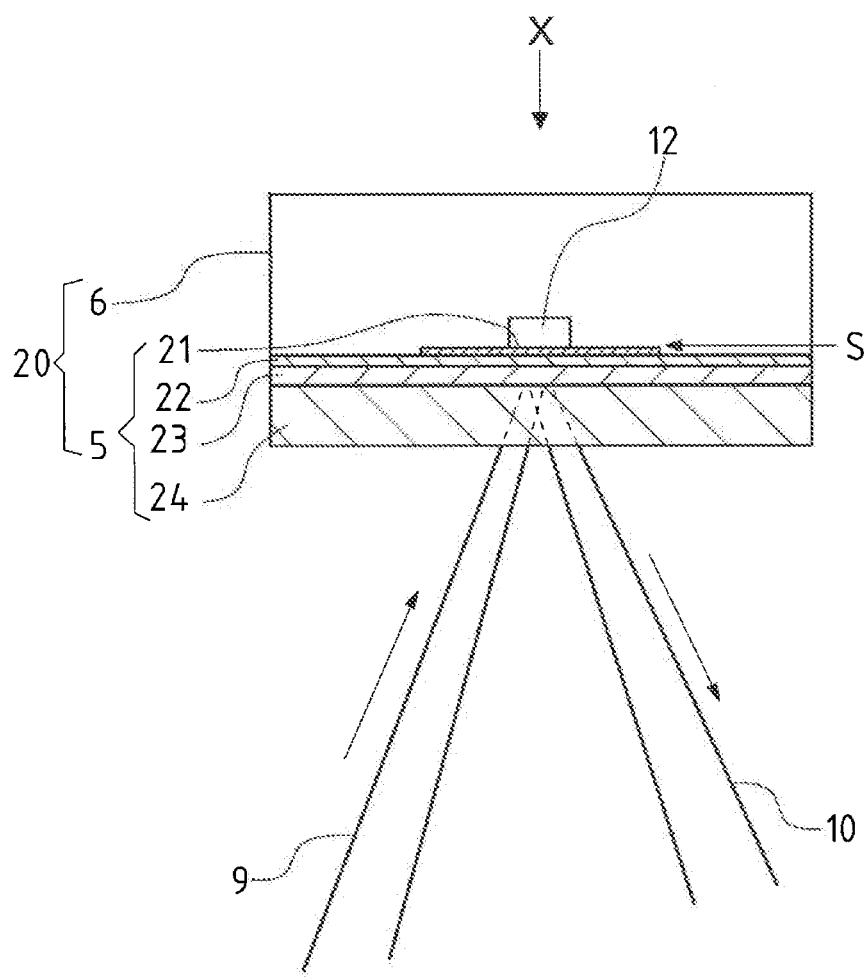
FIG. 5 is a cross sectional view of the same.

As shown in FIGS. 4 and 5, in the substance detecting plate 5, the plate-shaped flow path forming portion 6 is laminated integrally on the substance sensitive film 21. The flow path forming portion 6 incorporates the flow path 12 serving as a detected region having a crank shape in a side view and a reference region 13. The flow path 12 and the reference region 13 has a rectangular cross section (refer to FIG. 7). The bottom being a part of the inner wall surface of the flow path 12 is formed by the surface of the substance sensitive film 21. An interface S between the substance sensitive film 21 and the flow path forming portion 6 is in close contact so as to be sealed except a part of the substance sensitive film 21 used to form the bottom of the flow path 12 and the reference region 13. Similarly, the interface between the flow path forming portion 6 and the insulator 22 is in close contact so as to be sealed and is treated such that the solution is prevented from penetrating from the inside of the flow path 12 and the reference region 13 into the interface S. Specifically, in the case where the solution flows in the flow path 12 (a reference solution flows in the reference region 13) or is stored in the flow path 12 (the reference region 13), the solution comes in contact with the surface of the substance sensitive film 21 being the bottom portion of the flow path 12 (the reference solution comes in contact with the bottom portion of the reference region 13).

The shape of the flow path 12 is not particularly limited to the crank shape, and may be changed suitably in accordance with the type of a solution reaction or the like. Examples of the shapes of the flow path include straight shape, meander shape, and Y-shape.

The flow path forming portion 6 may be constituted such that a heating or cooling means is disposed in the vicinity of the flow path 12.

As shown in FIG. 4, a solution including a detection object substance is injected through a solution inlet 32, and the solution no longer necessary after inspection is discharged through a solution outlet 33.

Figure 6:
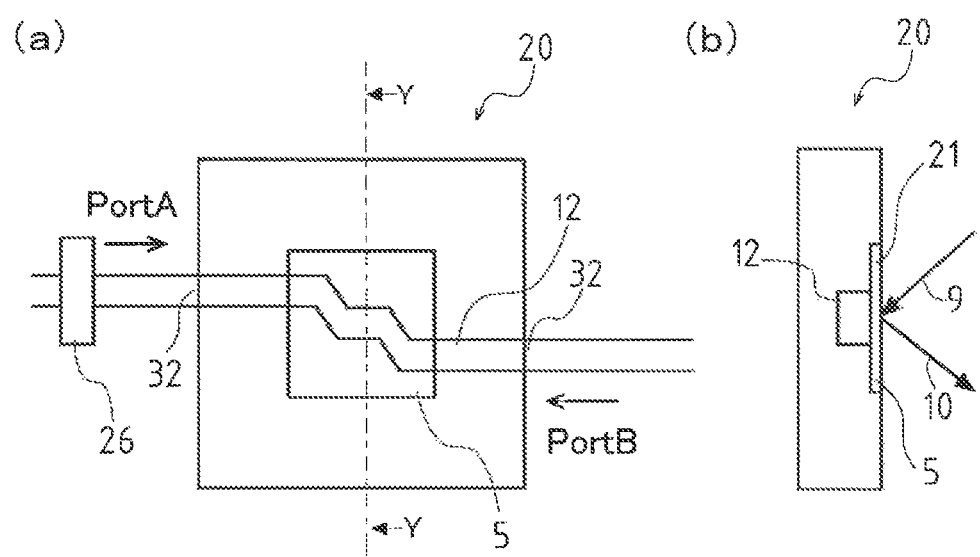
FIG. 6 is a schematic diagram showing a measurement area of a solution concentration distribution measuring device, in which (a) is a diagram viewed in an arrow X in FIG. 5, and (b) is a cross sectional taken along the line Y-Y in (a).

As shown in FIG. 6, a reference electrode 26 serving as a means for stabilizing the electric potential of the solution is interposed at a predetermined position on an intermediate portion of a solution supply pipe coupled to the solution inlet 32. The reference electrode 26 is a silver-silver chloride electrode soaked in a potassium chloride-saturated solution, and is structured such that the silver-silver chloride electrode is put in a glass tube in which the potassium chloride-saturated solution is enclosed. A voltage source is arranged between the reference electrode 26 and the above-mentioned lead wire 25 so that a voltage can be applied, and the reference electrode 26 is configured to function as a means for stabilizing the electric potential of the solution including the detection object substance.

In this regard, the reference electrode 26 is disposed as a preparatory device in the constitution of the measuring device 1, and is unnecessary in the case where the reference region 13 is used. Accordingly, the measuring device 1 may be constituted without disposing the reference electrode 26 and the lead wire 25.

The controlling and analyzing device 8 controls the pulsed laser beam source 2 so as to radiate the pulsed laser beam 9 onto a position that is opposite to the insulator 22 in the semiconductor 23 of the substance detecting plate 5 and corresponds to the substance sensitive film 21. The pulsed electromagnetic wave 10 generated by the radiation of the pulsed laser beam 9 is detected by the detecting and converting device 4, and the controlling and analyzing device 8 is configured to take in the detection result so as to detect existence or absence of a reaction in the substance sensitive film 21 and the degree of the reaction based on the amplitude strength of the pulsed electromagnetic wave 10.

While continuing the detection of the pulsed electromagnetic wave 10 for the substance sensitive film 21, the controlling and analyzing device 8 controls the scanning table 7 so as to move the measurement plate 20, thereby radiating the pulsed laser beam 9 onto the semiconductor 23 corresponding to the substance sensitive film 21 in the flow path 12. Thus, the solution concentration distribution measuring device 1 includes a means (the scanning table 7, the pulsed laser beam source 2) for radiating the pulsed laser beam 9 in a two-dimensional scanning manner. Accordingly, the measuring device 1 can radiate the pulsed laser beam 9 continuously onto the substance sensitive film 21 (the semiconductor 23) by the means (the scanning table 7, the pulsed laser beam source 2) for radiating the pulsed laser beam 9 in a two-dimensional scanning manner, and can measure continuously the amplitude strength of the pulsed electromagnetic wave 10 generated by the irradiation.

Although the measuring device 1 includes the means (the scanning table 7, the pulsed laser beam source 2) for radiating the pulsed laser beam 9 in a two-dimensional scanning manner, scanning is not necessarily conducted at the time of measurement. Accordingly, necessity or unnecessity of the scanning may be judged in accordance with the measurement environment so as to use the scanning means appropriately.

The controlling and analyzing device 8 functions as a means for measuring the detection object substance qualitatively or quantitatively based on the amplitude strength of the pulsed electromagnetic wave 10 and to acquire reaction distribution or concentration distribution of the substance in the solution in the flow path 12. Accordingly, the controlling and analyzing device 8 detects existence or absence of a reaction in each substance sensitive film 21 (existence or absence of a change of the electromagnetic wave amplitude strength) and the degree of the reaction (the change amount of the electromagnetic wave amplitude strength). Based on these detection results, the controlling and analyzing device 8 further detects the reaction distribution or the concentration distribution in the solution, thereby analyzing the detection object substance.

Next, description will be given for a measuring method employed in the measuring device 1 constituted as mentioned above and is configured to use a pulsed electromagnetic wave.

Figure 8:
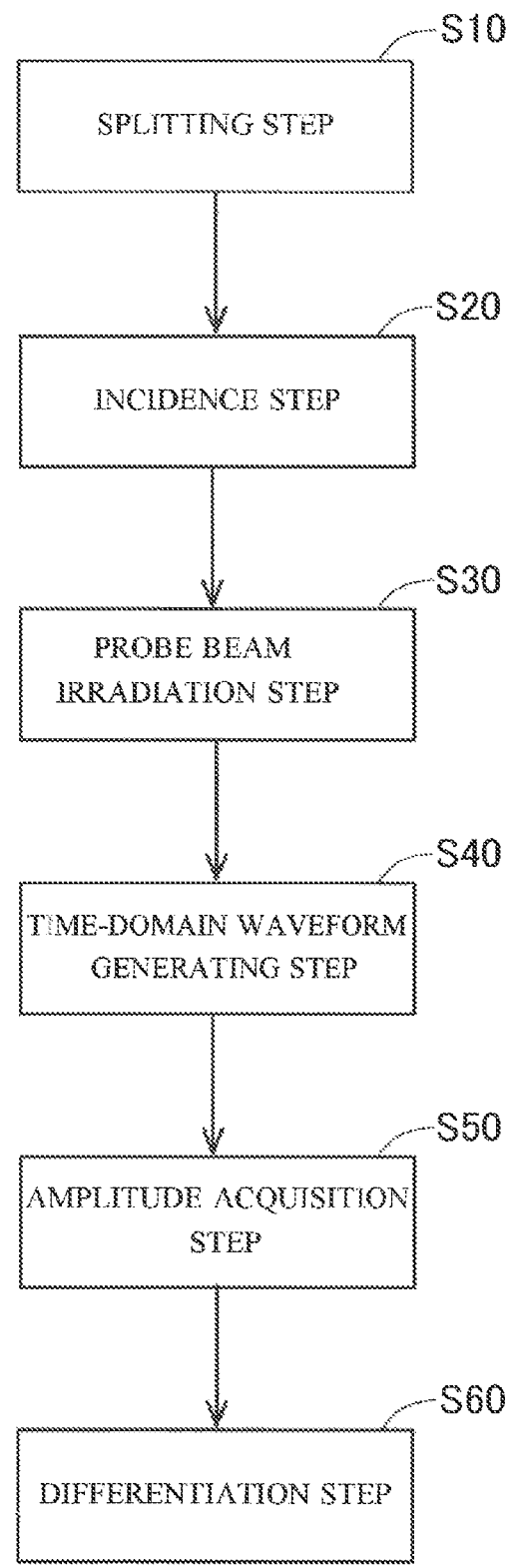
FIG. 8 is a flow chart showing a flow of a measuring method the use a pulsed electromagnetic wave.

The measuring method configured to use the pulsed electromagnetic wave according to this embodiment proceeds in accordance with a flow shown in FIG. 8, and includes a splitting step S10, an incidence step S20, a probe beam irradiation step S30, a time-domain waveform generating step S40, an amplitude acquisition step S50, and a differentiation step S60.

First, as shown in FIG. 1, the substance detecting plate 5 is placed at a predetermined position on the scanning table 7. The control and analyzing apparatus 8 performs control so that the substance detecting plate 5 (a measurement plate 20) is moved on the scanning table 7 such that the irradiated position of the pulsed laser beam 9 matches a predetermined position (start position) of the substance sensitive film 21 serving as the bottom of both the flow path 12 and the reference region 13. Then, the pulsed laser beam 9 is radiated from the pulsed laser beam source 2.

In the splitting step S10 the pulsed laser beam 9 is split into two beams of the probe beam L1 and the pump beam L2.

That is, in the splitting step S10, in FIG. 1, the pulsed laser beam 9 output from the pulsed laser beam source 2 is split by the second beam splitter 14 (in this embodiment, a half mirror) into two pulsed laser beams 9 of the probe beam L1 and the pump beam L2.

In the incidence step S20, the pump beam L2 is split into two. Then, one split pump beam L2 of the two pump beams L2 is radiated onto the semiconductor 23 corresponding to the flow path 12 serving as a detected region into which a solution containing the detection object substance can be introduced. In addition, the other split pump beam L2 of the two pump beams L2 is radiated onto the semiconductor 23 corresponding to the reference region 13 into which a reference solution can be introduced. Successively, the pulsed electromagnetic waves 10a and 10b generated from positions of the semiconductor 23 corresponding respectively to the flow path 12 and the reference region 13 are focused and made incident on the detecting element 19 serving as a single detecting means.

Specifically, in the incidence step S20, the pump beam L2 being one beam of the pulsed laser beams 9 split by the beam splitter 14 passes through the mirror 29, the optical chopper 16, the mirror 30, and the lens 350. As shown in FIG. 7, the pump beam L2 passed through the optical chopper 16 is split into two pump beams L2 by the first beam splitter 17. Then, one pump beam L2 of the two pump beams L2 is radiated onto the semiconductor 23 corresponding to the flow path 12 serving as the detected region, and the other pump beam L2 of the two pump beams L2 is radiated onto the semiconductor 23 corresponding to the reference region 13. Successively, the pulsed electromagnetic waves 10a and 10b generated from the positions of the semiconductor 23 corresponding respectively to the flow path 12 and the reference region 13 as the respective irradiated positions of the two pump beams L2 are focused to one end of the detecting element 19 by the off-axis parabolic mirror serving as the focusing means 18. Then, the amplitude intensity of each of the pulsed electromagnetic waves 10a and 10b generated by irradiation of the pump beams L2 is detected by the detecting element 19.

In the probe beam irradiation step S30, the probe beam L1 passes through the time delaying means 15, and is radiated onto the detecting element 19 in synchronization with the timing at which the pulsed electromagnetic waves 10a and 10b generated by the respective pump beams L2 are made incident.

That is, in the probe beam irradiation step S30, the probe beam L1 being one beam of the pulsed laser beams 9 split by the beam splitter 14 is radiated onto other end of the detecting element 19 via the time delaying means 15, a mirror 31, a mirror 34, and a lens 35. At this time, the probe beam L1 is radiated in synchronization with a timing when the pulsed electromagnetic waves 10a and 10b generated from the semiconductors 23 corresponding to the flow path 12 and the reference region 13 are made incident on the detecting element 19.

In the time-domain waveform generating step S40, the amplitude intensity of each of a plurality of the pulsed electromagnetic waves 10 different in delay time corresponding respectively to the flow path 12 and the reference region 13 in synchronization with the probe beam L1 are acquired, thereby producing time-domain waveforms of the pulsed electromagnetic waves 10 corresponding to the flow path 12 and the reference region 13.

Figure 9:
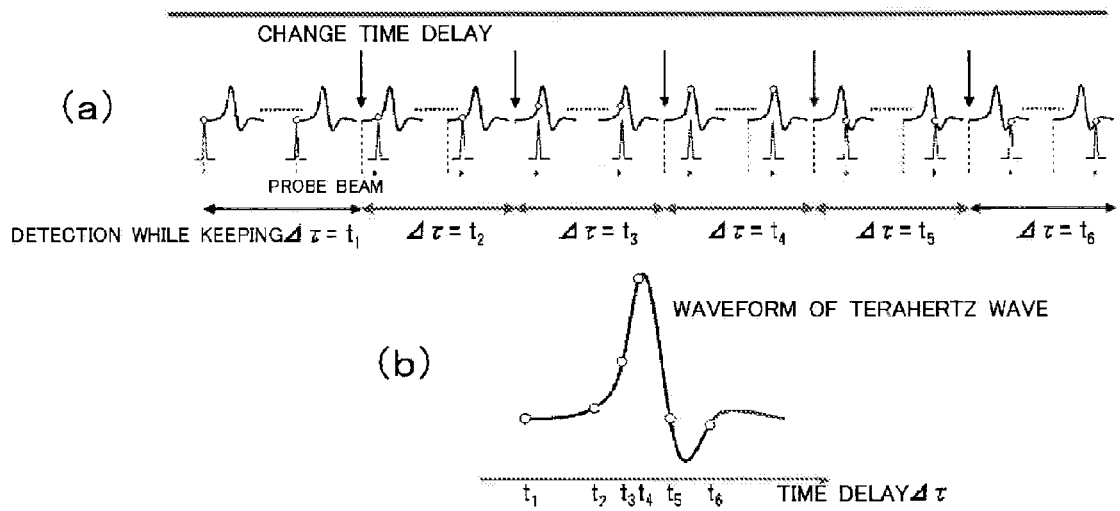
FIG. 9 is a diagram for describing a method for producing a time-domain wave.

That is, in the time-domain waveform generating step S40, the probe beam L1 split by the second beam splitter 14 passes through the time delaying means 15 in the optical path leading the detecting element 19. At this time, in the time delaying means 15, the probe beam L1 is made incident on and reflected from the movable mirror 15a arranged to be movable in a predetermined direction (in this embodiment, the direction parallel to the probe beam L1). The controlling and analyzing device 8 is configured to make the movable mirror 15a reciprocate periodically in the predetermined direction with a predetermined frequency, thereby delaying optically the arrival time of the probe beam L1 at the detecting element 19. In this way, the controlling and analyzing device 8 delays the timing at which the probe beam L1 is incident on the detecting element 19 while changing periodically the arrival time of the probe beam L1 at the detecting element 19 by time delaying means 15, whereby it becomes possible to acquire the amplitude intensity of the pulsed electromagnetic wave 10 at the incident timing of the probe beam L1 in predetermined time series (refer to FIG. 9 (a)).

Specifically, the controlling and analyzing device 8 produces the time-domain waves of the amplitude intensity based on the detected amplitude intensity of each of the pulsed electromagnetic waves 10. In this process, first, the pulsed electromagnetic waves 10a and 10b generated from the respective irradiated positions of the pump beams L2 on the substance detecting plate 5 are focused onto the detecting element 19. At this time, the probe beam L1 is radiated onto a predetermined position on the detecting element 19 in synchronization with the incidence of the pulsed electromagnetic waves 10a and 10b, whereby an electric current proportional to the electric field strength (amplitude intensity) of the electromagnetic wave 10 made incident at the time of the radiation of the probe beam L1 is generated. The electric current is converted into an electric voltage by the current amplifier 27, and then, the resulting electric voltage is subjected to lock-in detection by the lock-in amplifier 28 in synchronization with the chopping by the optical chopper 16. Successively, the detected value of the lock-in detection is input to the computer 8. Accordingly, it becomes possible to detect the amplitude intensity of each of the pulsed electromagnetic waves 10a and 10b made incident at the time of radiation of the probe beam L1 onto the detecting element 19.

Figure 10:
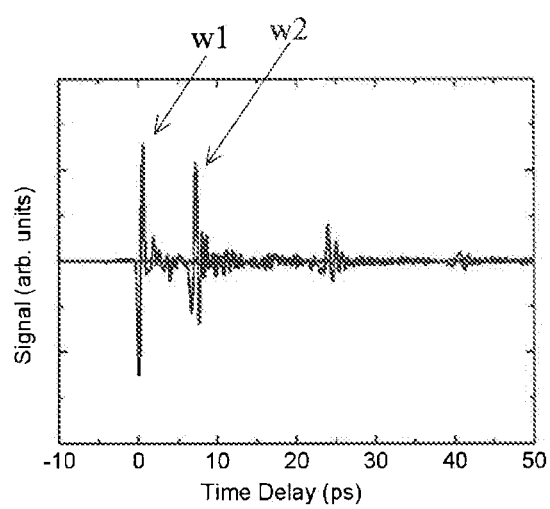
FIG. 10 is a diagram showing an amplitude intensity wave of each of pulsed electromagnetic waves respectively generated from the detected region and the reference region.

In the case where the wave of the pulsed electromagnetic wave 10 (for example, terahertz wave) made incident on the detecting element 19 forms a waveform shown in FIG. 9(b), a time delay $\Delta\tau$ being a time period necessary for the probe beam L1 to reach the detecting element 19 is changed by moving periodically the movable mirror 15a of the time delaying means 15, whereby a plurality of the probe beams L1 different in delay time are made incident on the detecting element 19. That is, as shown in FIG. 9(a), the entrance time of the probe beam L1 is delayed so as to acquire the amplitude intensity of each of the pulsed electromagnetic waves 10a and 10b at each of the time delays ($\Delta\tau$=t1, t2, t3, t4, t5, t6). As a result, a discrete signal chain indicated with the mark of "○" in FIG. 9(b) can be acquired. In FIG. 9(b), the horizontal axis represents a time delay $\Delta\tau$. The detection of the pulsed electromagnetic waves 10 in response to each of the plurality of the probe beams L1 different in this delay time enables to acquire the time-domain wave of each of the pulsed electromagnetic waves 10a and 10b as shown in FIG. 10. In the waveforms shown in FIG. 10, a waveform located at the left side is a waveform w1 related to the detected region (flow path 12), and a waveform located at the right side is a waveform w2 related to the reference region 13.

In the amplitude acquisition step S50, an amplitude intensity in each wave peak position is acquired from the time-domain waveforms that are produced in the time-domain waveform generating step S40 and correspond respectively to the flow path 12 and the reference region 13.

Specifically, in the amplitude acquisition step S50, the acquired time series waveforms w1 and w2 (refer to FIG. 10) corresponding respectively to the flow path 12 and the reference region 13 are subjected to predetermined arithmetic processing by the computer 8, thereby acquiring the amplitude intensity in a peak position of each of the flow path 12 and the reference region 13.

In the differentiation step S60, a difference is acquired between an amplitude intensity in the waveform peak position of the flow path 12 (the peak position of the waveform w1 related to the detected region (the flow path 12) located at the left side in FIG. 10) and an amplitude intensity in the waveform peak position of the reference region 13 (the peak position of the waveform w2 related to reference region 13 located at the right side in FIG. 10).

That is, in the differentiation step S60, a difference is acquired between the amplitude intensity corresponding to the solution containing the detection object substance introduced into the flow path 12 and the amplitude intensity corresponding to the reference solution introduced into the reference region 13.

In this way, the characteristics (change of the state of the solution) of the solution containing the detection object substance are measured. Hereafter, the measurement example of a specific detection object substance is shown.

Next, description will be given for a difference in detection results between the case where the measuring method configured to use the pulsed electromagnetic wave is employed in the above-mentioned measuring device 1 and the case where the measuring method is not employed.

Figure 11:
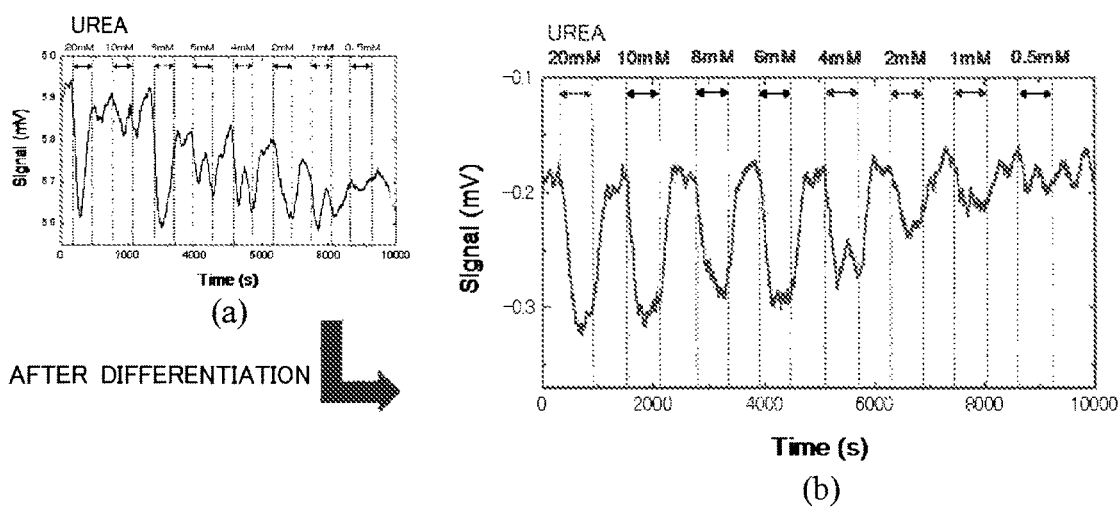
FIG. 11 is a diagram for describing noise cancellation in a differentiation step, in which (a) shows a graph before the differentiation, and (b) shows a graph after the differentiation.

FIG. 11 shows a change in the concentration of ammonia caused by the following mechanism. Specifically, when a urea solution stored in the flow path 12 is subjected to the catalytic action of a substance sensitive film 21 containing urease (enzyme), urea is hydrolyzed by the catalytic action, and ammonia is generated and thus, the concentration of urea in the solution decreases.

Specifically, FIG. 11(a) shows a change in the concentration of urea in the case where the measuring method that uses the pulsed electromagnetic wave 10 according to this embodiment is not employed in the measuring device 1, and FIG. 11(b) shows a change in the concentration of urea in the case where the measuring method that uses the pulsed electromagnetic wave 10 according to this embodiment is employed in the measuring device 1.

According to the comparison between FIG. 11(a) and FIG. 11(b), in the case (FIG. 11(a)) where the measuring method that uses the pulsed electromagnetic wave 10 according to this embodiment is not employed, since noises occur due to oscillation of the solution, dispersion appears in the relationship between the change in the concentration of urea and the amplitude intensity. On the other hand, in the case (FIG. 11(b)) where the measuring method that uses the pulsed electromagnetic wave 10 according to this embodiment is employed, since noises attributable to the solution are cancelled by the differentiation step S60, it turns out that the relationship between the change in the concentration of urea and the amplitude intensity changes almost proportionally (the amplitude intensity decreases in association with the decrease of the concentration). Thus, when the measuring method that uses the pulsed electromagnetic wave according to this embodiment is employed in the measuring device 1, noises attributable to the solution are cancelled, whereby detection sensitivity and detection accuracy can be improved dramatically.

Further, the measurement of the time change of the amplitude intensity enables to analyze chemical reactions caused between a detection object substance and a sensitive film, a reaction rate of a binding reaction, and a binding constant. For example, in the case where the measurement is achieved by use of an antibody protein as the sensitive film and by use of an antigen as the detection object substance and a graph is produced based on the measurement on the condition that the vertical axis represents the amplitude intensity and the horizontal axis represents time, the binding constant can be determined from the time taken from the start of the reaction to the completion of the reaction and the inclination of the graph.

Furthermore, in a series of above analyses, once the measurement plate 20 is set, by moving the measurement plate 20 on the scanning table 7 and radiating the pulsed laser beam 9 continuously, the analyses can be achieved for the detection object substance on the entire area of the bottom in the flow path 12. Therefore, a large amount of analysis data can be acquired with excellent workability and efficiently in a short time. In addition, since the reactions between the detection object substance and the substance sensitive film 21 can be detected directly, substance detection can be achieved in a label-free manner.

The measuring device 1 that uses the pulsed electromagnetic wave 10 according to this embodiment is configured to split the pulsed laser beam 9 by the first beam splitter 18 into two pulsed laser beams 9; to radiate the pump beam L2 being one split pulsed laser beam 9 of the two pulsed laser beams 9 onto the semiconductor 23 corresponding to the detected region; also radiate the probe beam L1 being the other split pulsed laser beam 9 of the two pulsed laser beams 9 onto the semiconductor 23 corresponding to the reference region 13; to focus the pulsed electromagnetic waves 10a and 10b generated from the semiconductor 23 corresponding to the detected region and the reference region by the focusing means 18; and to detect the resultant beam by the single detecting element 19. In the original study of the inventors, the following constitution is studied. A detected region and a reference region are disposed on a substance detecting plate 5. Then, the position of the substance detecting plate 5 is moved such that each of the detected region and the reference region is irradiated with a laser beam alternately, and the pulsed electromagnetic waves 10a and 10b generated by the irradiation are detected. However, in this constitution, although there is no need to move the laser and the optical system of the electromagnetic waves, the solution containing the detection object substance is agitated. Accordingly, the solution cannot be measured dynamically, and the time change of reaction cannot be detected precisely. Therefore, the inventors studied another constitution configured not to move the position of the substance detecting plate 5 and to include two pulsed laser systems to respectively emit a pulsed laser for a detected region and a pulsed laser for a reference region. However, in such another constitution, it is necessary to prepare two independent systems each including a laser and an optical system for electromagnetic waves. Accordingly, there is concern that cost, size of a device, performance decrement in control ability and the like might occur. Thus, the inventors has arrived at the configuration of the present invention in which the single pulsed laser beam 9 is split into two pulsed laser beams 9, the two pulsed laser beams 9 are radiated simultaneously respectively onto a detected region and a reference region, and the pulsed electromagnetic waves 10a and 10b generated from the respective irradiated positions of the detected region and the reference region are focused onto a single detecting means by a parabolic mirror. Moreover, at the time of detection for the detected region and the reference region by the single detecting means, a difference in position is captured as a difference in detection time (delay time), and then, waveforms related to the respective pulsed electromagnetic waves 10a and 10b are measured separately from each other (refer to FIG. 10), whereby it becomes possible to achieve the measurement by the device constitution according to the invention. In this way, according to the measuring device and measuring method that uses the pulsed electromagnetic wave in this embodiment, the detection sensitivity and the detection accuracy of the measuring device can be improved.

The present invention should not be limited to the above-mentioned embodiment. That is, based on the gist of the present invention, various modifications can be made. The various modifications are not excluded from the scope of the present invention.

Figure 13:
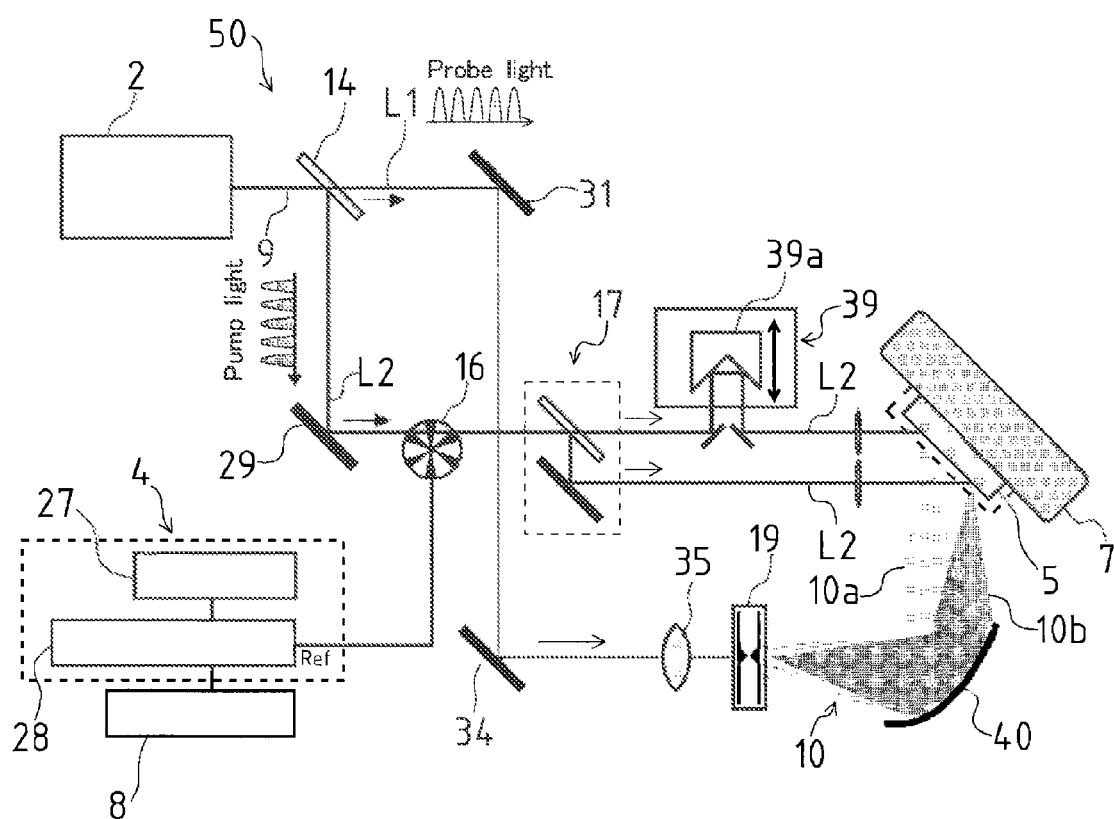
FIG. 13 is a schematic diagram of a measuring device that uses a pulsed electromagnetic wave according to the second embodiment of the present invention.

FIG. 13 shows a second embodiment of the measuring device that uses pulsed electromagnetic waves according to the present invention. A principle according to the present invention and used by the measuring device that uses pulsed electromagnetic waves according to the second embodiment is the same with the above-mentioned principle. In the measuring device that uses pulsed electromagnetic waves according to the second embodiment, parts common to the parts of the measuring device 1 described in the first embodiment and portions having respective common functions are indicated by the same reference sign, and duplicated description thereof is omitted.

A solution concentration distribution measuring device 50 (hereafter, referred to as a measuring device 50) is a measuring device that uses pulsed electromagnetic waves 10, and includes a substance detecting plate 5 (sensing plate), a flow path 12 (refer to FIG. 14), a reference region 13 (refer to FIG. 14), a stabilizing means (below-mentioned reference electrode 26), a generating means (pulsed laser beam source 2), a second beam splitter 14, an radiating means (scanning table 7, pulsed laser beam source 2), a measuring means (detecting and converting device 4), a pulse timing adjusting device 15, and an acquiring means (controlling and analyzing device 8). The substance detecting plate 5 includes a semiconductor 23, an insulator 22 formed on the semiconductor 23, and a substance sensitive film 21 formed on the insulator 22. The flow path 12 is disposed on the insulator 22 (substance sensitive film 21), a solution containing a detection object substance flows therethrough, and serves as a detecting region in which a solution containing a detection object substance can be introduced. The reference region 13 is disposed in the vicinity of the flow path 12 on the insulator 22 (substance sensitive film 21), and a reference solution can be introduced therein. The stabilizing means (reference electrode 26) is configured to stabilize the electric potential of a solution. The generating means (pulsed laser beam source 2) is configured to radiate a pulsed laser beam 9 onto a position corresponding to the flow path on the substance detecting plate 5 from the semiconductor 23 side being an opposite side of the insulator 22, thereby generating a pulsed electromagnetic wave 10 having an amplitude intensity corresponding to an amount of the detection object substance at the irradiated position. The second beam splitter 14 is configured to split the pulsed laser beam 9 radiated by the pulsed laser beam source 2 into two beams of a probe beam L1 and a pump beam L2. The radiating means (scanning table 7, pulsed laser beam source 2) is configured to radiate the pulsed laser beam 9 in a two-dimensional scanning manner. The measuring means (detecting and converting device 4) is configured to measure the amplitude intensity of the pulsed electromagnetic wave 10. The pulse timing adjusting device 39 is disposed on an optical path of the pump beam L2 between the first beam splitter 17 and the semiconductor 23 included in the substance detecting plate 5, and serves as a pulse timing adjusting means capable of adjusting the pulse timing of the pump beam L2 as desired. The acquiring means (controlling and analyzing device 8) is configured to measure the detection object substance qualitatively or quantitatively from the amplitude intensity, thereby acquiring the reaction distribution or concentration distribution of the substance in the solution in the flow path 12. Further, in this embodiment, the below-mentioned substance sensitive film 21 constitutes a part (in this embodiment, a bottom portion of the inner wall surface of the flow path 12) of the inner wall surface of the flow path 12 in a flow-path forming portion 6. Hereafter, the details of a device constitution will be described.

The controlling and analyzing device 8 is not particularly limited to the acquiring means for acquiring the reaction distribution or concentration distribution of substances in a solution, and may be a means for measuring the characteristics of a solution containing the detection object substance, a change of the characteristics, and a change in the state of a solution. Further, examples of "the change in the state of a solution" that can be measured by the solution concentration distribution measuring device (the measuring device 1 and the measuring device 50) in this embodiment, includes a change in the ion concentration of a solution, a change in the progress state of an antigen-antibody reaction in a sample solution (examples of the sample solution include blood, body fluid, and other solutions including antigens), and a change in each of the various chemical reaction states in a solution. In addition, a change of each of the above changes over time is also included.

Furthermore, in this embodiment, a portion located at the substance detecting plate 5 side in an inner wall surface of the flow path 12 is called a bottom portion for convenience sake.

On the basis of the above-mentioned principle, the detection object substance is detected by the device constitution of the measuring device 50 shown in FIG. 13 according to the second embodiment.

FIG. 13 is a schematic drawing of the solution concentration distribution measuring device in this embodiment. As shown in this drawing, the solution concentration distribution measuring device 50 in this embodiment includes a radiating device (optical system), the detecting and converting device 4 and the controlling and analyzing device 8.

In FIG. 13, the radiating device (optical system) mainly includes the pulsed laser beam source 2, the second beam splitter 14, the light beam chopper 16, the pump beam splitting and focusing means (the first beam splitter 17 (refer to FIG. 14), a focusing means 40), a pulse timing adjusting device 39, and the scanning table 7. The radiating device (optical system) has a function to radiate the pulsed laser beam 9 (pump beam L2) having a predetermined wavelength onto the flow path 12 as the detected region and to the reference region 13 disposed at predetermined positions on the substance detecting plate 5.

The constitution of mirrors and the like used for changing the direction of the pulsed laser beam 9 is not be limited to that in this embodiment, and the constitution may be changed appropriately, for example, the number of mirrors may be increased, in consideration of the arrangement of each of the constitutional components.

Figure 15:
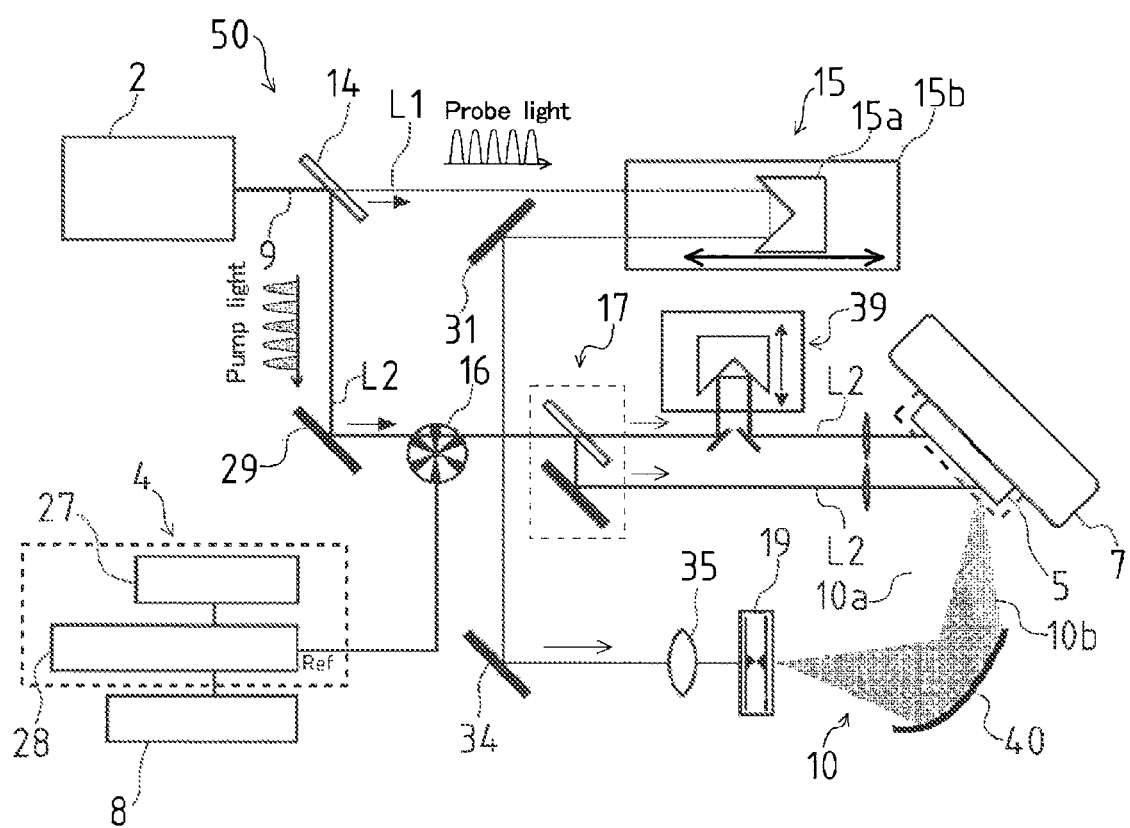
FIG. 15 is a schematic diagram of a measuring device that uses a pulsed electromagnetic wave according to the present invention (in the case where a pulse timing adjusting means and a time delaying means are used together).

Further, as shown in FIG. 15, the radiating device (optical system) may be constituted so as to include the time delaying means 15 in the optical path of the probe beam L1. In the case where the time delaying means 15 is disposed, the time delaying means 15 can be used at the time of periodical calibration of the measuring device. In the second embodiment, the measuring device 50 is constituted so as not to include the time delaying means 15.

Furthermore, the radiating device includes the scanning means for radiating the pulsed laser beam 9 in a two-dimensional scanning manner. Specifically, the scanning means has a function to radiate the pulsed laser beam 9 onto the substance detecting plate 5 on the scanning table 7 while causing the substance detecting plate 5 and the flow path forming portion 6 to reciprocate on the scanning table 7 (XY automatic stage) by a driving device (not shown).

As shown in FIG. 4, the pump beam L2 being a split light beam of the pulsed laser beam 9 is radiated onto the semiconductor 23 corresponding to the position of the substance sensitive film 21 constituting the bottom portion of the flow path 12 (radiated onto the flow path 12 located at one side surface portion of the flow path forming portion 6). The whole body of the substance detecting plate 5 and the flow path forming portion 6 laminated in a close contact state on the substance detecting plate 5 is moved by the scanning table 7 so that the semiconductor 23 corresponding to the substance sensitive film 21 on the bottom portion of the flow path 12 is moved to a position irradiated with the pump beam L2, whereby the laser beam-irradiated surface of the semiconductor 23 is scanned with the pump beam L2. By radiation of the pump beam L2, a pulsed electromagnetic wave 10 is generated continuously from the laser beam-irradiated position of the semiconductor 23.

The scanning constitution is not particularly limited to the constitution in this second embodiment. For example, the pulsed laser beam 9 may be made to scan two-dimensionally on the substance detecting plate 5 by a mirror (not shown) being oscillated or rotated or by radiation from the pulsed laser beam source 2 being oscillated.

As shown in FIG. 13, in this embodiment, the plane formed by the respective paths of the pulsed laser beam 9 and the pulsed electromagnetic wave 10 is an approximately horizontal plane. Specifically, FIG. 13 shows a constitution of a top view, and in the side view of this constitution, the pulsed laser beam 9 and the pulsed electromagnetic wave 10 are arranged to form an approximately horizontal plane. However, it is desirable to arrange them appropriately in accordance with the configuration and securing method of each device. Accordingly, it is not necessary to constitute such an approximately horizontal plane. Further, in this embodiment, the pump beam L2 split from the pulsed laser beam 9 is radiated onto the semiconductor 23 corresponding to one side of the flow path 12 (in this embodiment, the bottom side of the flow path 12) of the flow path forming portion 6.

The incident angle of the pump beam L2 being a split light beam of the pulsed laser beam 9 on the substance detecting plate 5 is preferably an angle at which the wavelength of the pulsed laser beam 9 is most absorbed by the semiconductor 23 of the substance detecting plate 5. However, depending on the configuration and securing method of each device, the incident angle is not necessarily limited to this angle, and is not particularly limited.

The second beam splitter 14 serves as a means for splitting the pulsed laser beam 9 incident thereon into a probe beam L1 and a pump beam L2. In this embodiment, as the second beam splitter 14, a half mirror capable of splitting the pump beam L2 in the direction perpendicular to the probe beam L1 going straight ahead is employed.

The optical chopper 16 is disposed on the optical path of the pump beam L2 (in this embodiment, the optical path between a mirror 29 and a first beam splitter 17), and can chop the pump beam L2 with a predetermined frequency.

Figure 14:
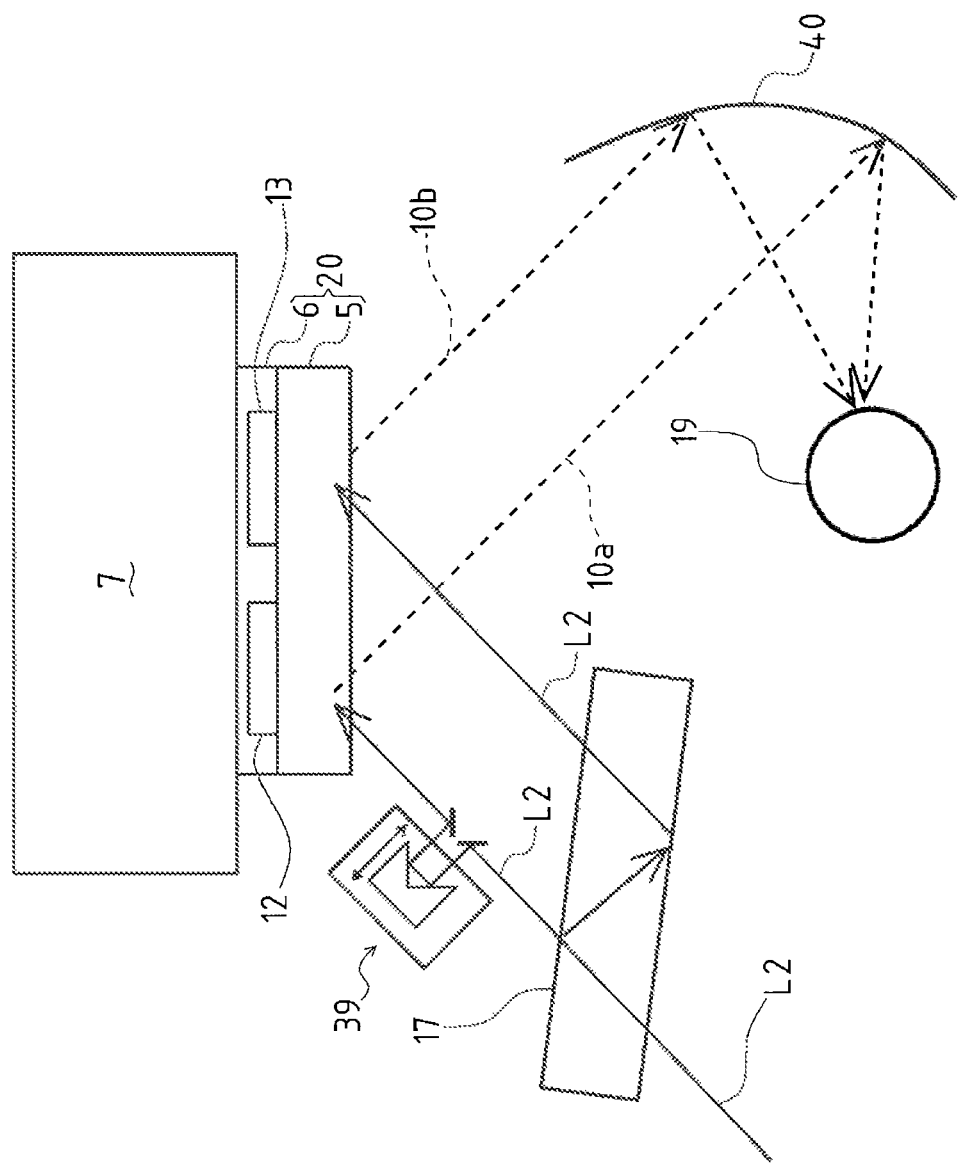
FIG. 14 is an illustration showing a substance detecting plate that includes a detected region and a reference region.

As shown in FIG. 14, the pump beam splitting and focusing means includes the first beam splitter 17 to split the entering pump beam L2 into two parallel pump beams L2 and an off-axis parabolic mirror serving as a focusing means 40 for focusing two pulsed electromagnetic waves 10a and 10b generated by the two parallel pump beams L2. The first beam splitter 17 according to this embodiment is a beam splitter of a parallel flat plate mirror type sown in FIG. 12(b), and can split the pump beam L2 going straight ahead into two parallel pump beams L2. This pump beam splitting and focusing means is configured to split the pump beam L2 being the pulsed laser beam 9 into two parallel pump beams L2 via the first beam splitter 17, to radiate one split pump beam L2 of the two parallel pump beams L2 onto the semiconductor 23 corresponding to the flow path 12 as a detected region, and to further radiate the other split pump beam L2 onto the semiconductor 23 corresponding to the reference region 13.

Among the respective optical paths of the two pump beams L2 before the two parallel pump beams split by the first beam splitter 17 are radiated onto the semiconductor 23, in the optical path of one pump beam L2 (in FIG. 13, the optical path of the pump beam L2 shown at the upper side among the two pump beams L2), the pulse timing adjusting device 39 is disposed.

The pulse timing adjusting device 39 may be disposed on the optical path of either one of the two parallel pump beams L2 split by the beam splitter 17.

In FIG. 13, the detecting and converting device 4 includes the detecting element 19 serving as a detecting means, and a below-mentioned converting means. The detecting and converting device 4 is configured to detect the pulsed electromagnetic waves 10a and 10b that are emitted from the respective irradiated positions of the pulsed laser beams 9 (pump beams L2) on the semiconductor 23 and focused by the off-axis parabolic mirror serving as a focusing means 40, and to convert them to respective voltage signals each of which changes along time in response to the time wave of the electric field amplitude of the corresponding pulsed electromagnetic wave 10.

The detecting element 19 includes a photoconductive antenna or the like, and is disposed in such a manner that the pulsed electromagnetic waves 10a and 10b emitted from the respective irradiated positions of the pump beams L2 on the substance detecting plate 5 can be incident thereon. When the probe beam L1 is radiated onto a predetermined position on the detecting element 19 in synchronization with the incidence of one of the pulsed electromagnetic waves 10a and 10b, the detecting element 19 generates a current proportional to the electric field strength (amplitude intensity) of the one of the pulsed electromagnetic waves 10a and 10b incident thereon at the time of radiation of the probe beam L1.

The converting means includes a current amplifier 27 coupled to the detecting element 19 and a lock-in amplifier 28 coupled to the current amplifier 27. Further, the lock-in amplifier 28 is coupled to the optical chopper 16. This converting means can detect the amplitude intensity of one of the pulsed electromagnetic waves 10a and 10b incident thereon at the time of radiation of the probe beam L1 onto the detection element 19 by measuring the current generated by the detecting element 19. The frequency components included in the pulsed electromagnetic waves 10a and 10b are included within a range of from 10 GHz to 100 THz, whereby the detecting and converting device 4 with general constitutions can be utilized.

The controlling and analyzing device 8 is a device configured to detect existence or absence of the detection object substance (qualitative measurement), quantitative measurement of the detection object substance, and measurement of reaction distribution and concentration distribution of the detection object substance from the voltage signals converted by the converting means of the detecting and converting device 4, and to further perform analytical processing such as predetermined analysis by use of the time-domain wave of the amplitude intensity (voltage value) of the pulsed electromagnetic wave 10 and predetermined calculation. Further, in this embodiment, the controlling and analyzing device 8 serves as a computer capable of executing the control and analysis described in this specification, and, in addition, is configured to control the radiating device (optical system), the scanning table 7, the detecting and converting device 4, and the pulsed laser beam source 2 via control signal lines (not shown).

The controlling and analyzing device 8 controls the pulsed laser beam source 2 so that the pulsed laser beam 9 is radiated onto a position that is opposite to the insulator 22 in the semiconductor 23 of the substance detecting plate 5 and corresponds to the substance sensitive film 21. The pulsed electromagnetic wave 10 generated by the radiation of the pulsed laser beam 9 is detected by the detecting and converting device 4, and the controlling and analyzing device 8 is configured to take in the detection result so as to detect existence or absence of a reaction in the substance sensitive film 21 and the degree of the reaction based on the amplitude strength of the pulsed electromagnetic wave 10.

While continuing the detection of the pulsed electromagnetic wave 10 for the substance sensitive film 21, the controlling and analyzing device 8 controls the scanning table 7 so that the measurement plate 20 is moved and thus, the pulsed laser beam 9 is radiated onto the semiconductor 23 corresponding to the substance sensitive film 21 in the flow path 12. Thus, the measuring device 50 includes a radiating means (the scanning table 7, the pulsed laser beam source 2) for radiating the pulsed laser beam 9 in a two-dimensional manner. Accordingly, the measuring device 50 can radiate the pulsed laser beam 9 continuously onto the substance sensitive film 21 (the semiconductor 23) by the radiating means (the scanning table 7, the pulsed laser beam source 2) for radiating the pulsed laser beam 9 in a two-dimensional manner, and measure continuously the amplitude strength of the pulsed electromagnetic wave 10 generated by the radiation.

Although the measuring device 50 of this embodiment includes the radiating means (the scanning table 7, the pulsed laser beam source 2) for radiating the pulsed laser beam 9 in a two-dimensional manner, the scanning is not necessary conducted at the time of measurement. Accordingly, necessity or unnecessity of the scanning may be judged in accordance with the measurement environment so as to use the radiating means (the scanning table 7, the pulsed laser beam source 2) appropriately.

The controlling and analyzing device 8 functions as a measuring means for measuring the detection object substance qualitatively or quantitatively based on the amplitude strength of the pulsed electromagnetic wave 10 and to acquire reaction distribution or concentration distribution of the substance in the solution in the flow path 12. Accordingly, the controlling and analyzing device 8 detects existence or absence of a reaction in each substance sensitive film 21 (existence or absence of a change of the electromagnetic wave amplitude strength) and the degree of the reaction (the change amount of the electromagnetic wave amplitude strength). Based on these detection results, the controlling and analyzing device 8 further detects the reaction distribution or the concentration distribution in the solution, thereby analyzing the detection object substance.

Next, description will be given for a measuring method that uses pulsed electromagnetic waves employed in the measuring device 50 constituted as mentioned above according to the second embodiment.

Figure 16:
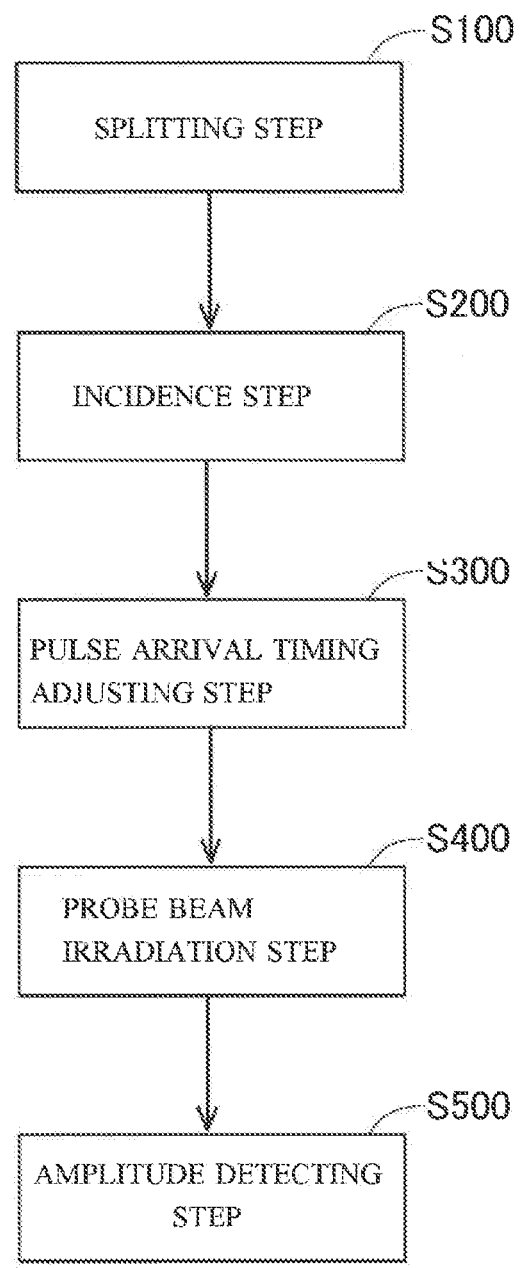
FIG. 16 is a flow chart showing a flow of a measuring method that uses a pulsed electromagnetic wave according to the second embodiment.

As shown in FIG. 16, the measuring method that uses the pulsed electromagnetic wave according to this embodiment includes a splitting step S100, an incidence step S200, a pulse arrival timing adjusting step S300, a probe beam irradiation step S400, and an amplitude detecting step S500.

First, as shown in FIG. 13, the substance detecting plate 5 is placed at a predetermined position on the scanning table 7. The control and analyzing apparatus 8 performs control so that the substance detecting plate 5 (the measurement plate 20) is moved on the scanning table 7 such that the position irradiated with the pulsed laser beam 9 matches a predetermined position (start position) of the substance sensitive film 21 serving as the bottom portion of both the flow path 12 and the reference region 13. Then, the pulsed laser beam 9 is radiated from the pulsed laser beam source 2.

In the splitting step S100, the pulsed laser beam 9 is split into two beams of a probe beam L1 and a pump beam L2.

That is, in the splitting step S10, in FIG. 13, the pulsed laser beam 9 output from the pulsed laser beam source 2 is split by the second beam splitter 14 (in this embodiment, a half mirror) into two pulsed laser beams 9 of the probe beam L1 and the pump beam L2.

In the incidence step S200, the pump beam L2 is split into two pump beams L2. Then, one split pump beam L2 of the two pump beams L2 is provided with a predetermined pulse timing adjusted by the pulse timing adjusting device 39, and then radiated onto the semiconductor 23 corresponding to the flow path 12 serving as a detected region into which a solution containing the detection object substance can be introduced. In addition, the other split pump beam L2 of the two pump beams L2 is radiated onto the semiconductor 23 corresponding to the reference region 13 into which a reference solution can be introduced. Successively, the pulsed electromagnetic waves 10*a* and 10*b* generated from positions of the semiconductor 23 respectively corresponding to the flow path 12 and the reference region 13 are focused and made incident on the detecting element 19 serving as a single detecting means.

Specifically, in the incidence step S200, the pump beam L2 being one beam of the pulsed laser beams 9 split by the beam splitter 14 passes through the mirror 29 and the optical chopper 16. Further, in the incidence step S200, as shown in FIGS. 13 and 14, the pump beam L2 passed through the optical chopper 16 is split into two pump beams L2 by the first beam splitter 17. Then, one pump beam L2 of the two pump beams L2 is provided with a predetermined pulse timing adjusted by passing through the pulse timing adjusting device 39, and radiated onto the semiconductor 23 corresponding to the flow path 12 serving as the detected region. In addition, the other pump beam L2 of the two pump beams L2 is radiated onto the semiconductor 23 corresponding to the reference region 13. Successively, the pulsed electromagnetic waves 10*a* and 10*b* generated from positions of the semiconductor 23 corresponding respectively to the flow path 12 and the reference region 13 as the respective irradiated positions of the two pump beams L2 are focused to one end of the detecting element 19 by the off-axis parabolic mirror serving as the focusing means 40, and made incident on the single detecting element 19.

This embodiment is constituted such that the pump beam L2 radiated onto the semiconductor 23 corresponding to the flow path 12 serving as the detected region passes through the pulse timing adjusting device 39. This should not be construed in a limiting sense. For example, the pump beam L2 radiated onto the semiconductor 23 corresponding to the reference region 13 may pass through the pulse timing adjusting device 39. Specifically, either one pump beam L2 of two pump beams L2 split by the beam splitter 17 may pass through the pulse timing adjusting device 39.

In the pulse arrival timing adjusting step S300, the pulse timing of one pump beam L2 of the two pump beams L2 is adjusted preliminarily such that the detection timings of the respective amplitude intensities of the pulsed electromagnetic waves 10*a* and 10*b* detected by the detecting element 19 match.

Specifically, in the pulse arrival timing adjusting step S300, the pulse timing of one pump beam L2 of the two pump beams L2 (in this embodiment, the pump beams L2 radiated onto the semiconductor 23 corresponding to the flow path 12) is adjusted preliminarily by the pulse timing adjusting device 39 disposed on the optical path of the pump beam L2 between the first beam splitter 17 and the semiconductor 23 such that the detection timings of the respective amplitude intensities of the pulsed electromagnetic waves 10*a* and 10*b* detected by the detecting element 19 match.

Specifically, in the measuring device 50, when one pump beam L2 of two parallel pump beams L2 split by the first beam splitter 17 passes through the pulse timing adjusting device 39 at an intermediate portion of the optical path leading to the semiconductor 23 of the substance detecting plate 5, the one pump beam L2 is made incident on an adjusting mirror 39*a* disposed to be adjustable in a predetermined direction (in this embodiment, a direction perpendicular to the probe beam L2), and is reflected by the adjusting mirror 39*a* in the pulse timing adjusting device 39. In the measuring device 50, at the time of measurement by use of the measuring device 50, the optical path length of one probe beam L1 can be adjusted by securing the adjusting mirror 39*a* included in the pulse timing adjusting device 39 at a predetermined position. Usually, the pulsed electromagnetic wave 10*a* generated from the semiconductor 23 corresponding to one probe beam L1 and the pulsed electromagnetic wave 10*b* generated from the semiconductor 23 corresponding to the other probe beam L2 are incident on the detecting element 19 at different timings. However, by moving the adjusting mirror 39*a* of the pulse timing adjusting device 39 so as to adjust the optical path length preliminarily, the arrival time (timing in the sense of optics) of the pulsed electromagnetic wave 10*a* at the detecting element 19 and the arrival time (timing in the sense of optics) of the pulsed electromagnetic wave 10*b* at the detecting element 19 can match. In this embodiment, by adjustment of pulse timings to match the detection timings, the amplitude intensities of the respective two pulsed electromagnetic waves 10*a* and 10*b* are detected at the same detecting timing by the detecting element 19. Accordingly, the amplitude intensity can be acquired in a state that the respective amplitude intensities of the two pulsed electromagnetic waves 10*a* and 10*b* are overlapped with each other.

The pulse arrival timing adjusting step S300 is not necessarily executed as the subsequent process of the entering step S200. For example, the pulse arrival timing adjusting step S300 may be performed appropriately regardless of other processes as needed, such as, at a measurement preparation stage before measurement by use of the measuring device 50 or at the time of monitoring of the measurement results of the measuring device 50 by a measuring operator or the controlling and analyzing device 8.

In the probe beam irradiation step S400, the probe beam L1 is radiated onto the detecting element 19 in synchronization with the timing at which each of the pulsed electromagnetic waves 10a and 10b generated by the respective pump beams L2 is made incident on the detecting element 19.

That is, in the probe beam irradiation step S400, the probe beam L1 being one beam of the pulsed laser beams 9 split by the beam splitter 14 is radiated onto the other end of the detecting element 19 via a mirror 31, a mirror 34, and a lens 35. At this time, the probe beam L1 is radiated in synchronization with a timing when each of the pulsed electromagnetic waves 10a and 10b generated from the semiconductor 23 corresponding respectively to the flow path 12 and the reference region 13 is made incident on the detecting element 19.

In the amplitude detecting step S500, the amplitude intensity of one of the pulsed electromagnetic waves 10a and 10b generated by the pump beam L2 and made incident on the detecting element 19 at the timing at which the probe beam L1 is radiated onto the detecting element 19 in the probe beam irradiation step S400.

Figure 17:
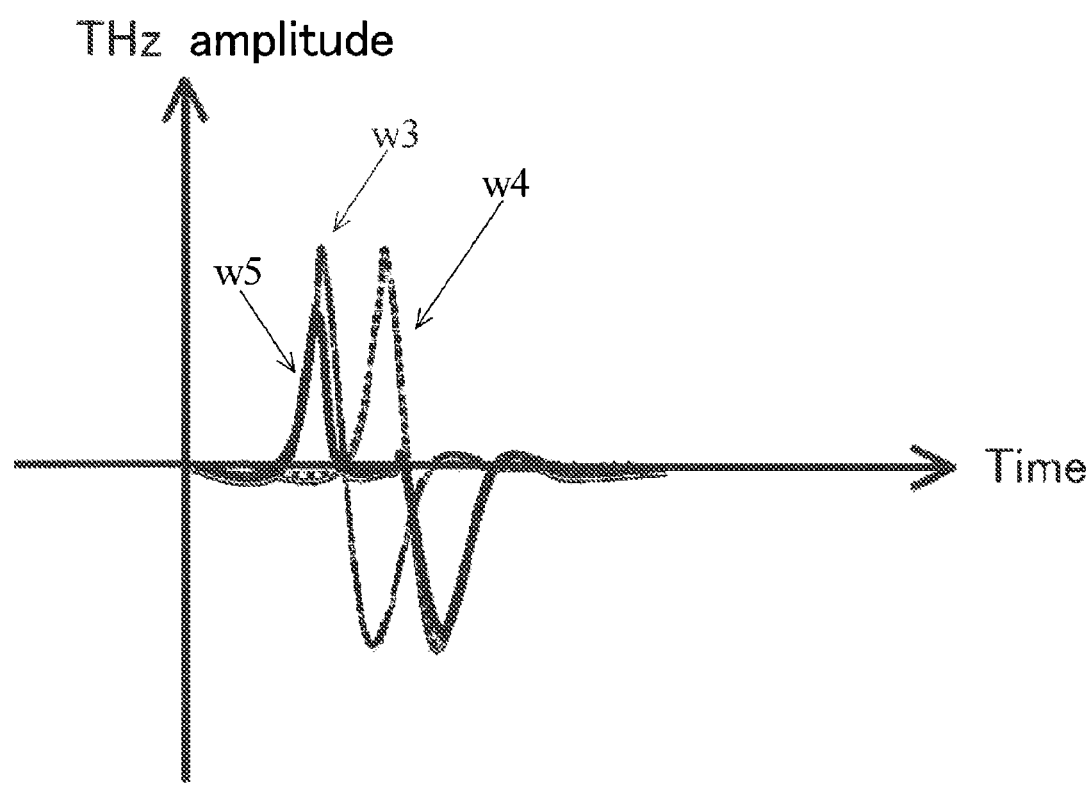
FIG. 17 is a diagram for describing a measuring method that uses a pulsed electromagnetic wave according to the second embodiment

Specifically, the controlling and analyzing device 8 is configured to detect the respective amplitude intensities of the pulsed electromagnetic waves 10a and 10. As the detecting step, first, the pulsed electromagnetic waves 10a and 10b generated from the respective irradiated positions of the pump beams L2 on the substance detecting plate 5 are focused onto the detecting element 19. At this time, the probe beam L1 is radiated onto a predetermined position on the detecting element 19 in synchronization with the timing at which the pulsed electromagnetic waves 10a and 10b are made incident, whereby an electric current proportional to the electric field strength (amplitude intensity) of the pulsed electromagnetic wave 10 made incident at the radiation timing is generated. The electric current is converted into an electric voltage by the current amplifier 27, and then, the resulting electric voltage is subjected to lock-in detection by the lock-in amplifier 28 in synchronization with the chopping by the optical chopper 16. Successively, the detected value of the lock-in detection is input to the computer 8. Accordingly, it becomes possible to detect the amplitude intensity of each of the pulsed electromagnetic waves 10a and 10b made incident at the timing at which the probe beam L1 is radiated on to the detecting element 19. In particular, in this embodiment, in the pulse arrival timing adjusting step S300, since the detection timings of the respective amplitude intensities of the pulsed electromagnetic waves 10a and 10b match, the respective amplitude intensities of the pulsed electromagnetic waves 10a and 10b are detected in the overlapped state. In this way, the controlling and analyzing device 8 can acquire a time-domain wave in the state that the pulsed electromagnetic waves 10a and 10b are made to overlap with each other as shown in FIG. 17. In FIG. 17, the vertical axis represents terahertz wave amplitude, and the horizontal axis represents time. In the waveform shown in FIG. 17, a left-side broken-line waveform is a waveform w3 related to the detected region (flow path 12), a right-side dot-line waveform is a waveform w4 related to the reference region 13, and a heavy-line waveform is a waveform 5 in which the waveform w3 and waveform w4 are made to overlap with each other. As shown in FIG. 17, the pulse timing of one pump beam L2 of the tow pump beams L2 is adjusted by the pulse timing adjusting device 39 such that the detection timing of the pulsed electromagnetic wave 10a due to the one pump beam L2 at the time of detection by the detecting element 19 matches the detection timing of the pulsed electromagnetic wave 10a due to the other pump beam L2 at the time of detection by the detecting element 19, whereby the respective amplitude intensities of the pulsed electromagnetic waves 10a and 10b can be acquired at the same timing. In FIG. 17, by overlapping the waveform w3 and the waveform w4, the waveform w4 related to the reference region 13 is canceled in the waveform w3 related to the flow path 12. Here, the detection timing adjusted by the pulse timing adjusting device 39 is a timing used to cancel the waveform w4 in the waveform w3. In this way, in the amplitude detecting step S500, both the amplitude intensity of the pulsed electromagnetic wave 10a and the amplitude intensity of the pulsed electromagnetic wave 10b are detected simultaneously by the detecting element 19 in a state that the amplitude intensity of the pulsed electromagnetic wave 10a generated by radiation of one pump beam L2 and the amplitude intensity of the pulsed electromagnetic wave 10b generated by radiation of the other pump beam L2 are made to overlap with each other. That is, the amplitude intensity of the pulsed electromagnetic wave 10b is subtracted from the amplitude intensity of the pulsed electromagnetic wave 10a so that a portion in which the amplitude intensity of the pulsed electromagnetic wave 10b is cancelled in the amplitude intensity of the pulsed electromagnetic wave 10a is detected. In the above way, the measuring device 50 measures the characteristics (a change in the state of a solution) of a solution containing the detection object substance.

In the case where the measuring method that uses the above pulsed electromagnetic wave 10 is not employed in the measuring device 50 according to this second embodiment, for example, an amplitude intensity is measured without removing noises due to fluctuation of the solution. On the other hand, in the case where the measuring method that uses the above pulsed electromagnetic wave 10 is employed in the measuring device 50 according to this second embodiment, it becomes possible to cancel noises attributable to the solution. Thus, when the measuring method that uses the above pulsed electromagnetic wave is employed in the measuring device 50 according to this second embodiment, the detection sensitivity and the detection accuracy can be improved dramatically by cancelling noises attributable to the solution.

As mentioned above, according to the present invention, the detection sensitivity and the detection accuracy of a measuring device can be improved.

Industrial Availability

According to the present invention, a device configured to detect interaction reactions (antigen-antibody, enzyme reaction, allergic reaction, and the like) between biological materials with high throughput can be obtained. Further, the present invention can be utilized widely in the fields, such as clinical examination, tailor-made medicine, medical studies, medicine development, environmental pollutant assessment, food safety management, and agricultural chemical examination.

What is claimed is:

1. A measuring device that uses a pulsed electromagnetic wave, comprising:
   a substance detecting plate including a semiconductor and an insulator formed on the semiconductor;
   a means configured to radiate a pulsed laser beam onto the substance detecting plate from a side of the semiconductor to generate a pulsed electromagnetic wave with an amplitude intensity depending on an amount of a detection object substance at an irradiated position; and a detecting means configured to detect the amplitude intensity of the pulsed electromagnetic wave, wherein the measuring device is configured to measure a change in a state of a solution containing the detection object substance from the amplitude intensity, the measuring device further comprising:
- a first beam splitter configured to split the pulsed laser beam into two beams;
- a detected region that is disposed on the insulator and into which a solution containing a detection object substance is able to be introduced; and
- a reference region that is disposed in a vicinity of the detected region on the insulator and into which a reference solution is able to be introduced, and wherein the pulsed laser beam is split into two split pulsed laser beams by the first beam splitter; one split pulsed laser beam of the two split pulsed laser beams is radiated onto the semiconductor corresponding to the detected region; the other split pulsed laser beam is radiated onto the semiconductor corresponding to the reference region; pulsed electromagnetic waves generated from the semiconductor corresponding to the detected region and the reference region are focused by a focusing means to be detected by the detecting means that is provided in singular.

2. The measuring device that uses the pulsed electromagnetic wave according to claim 1 further comprising:
- a second beam splitter configured to split the pulsed laser beam into two beams of a probe beam and a pump beam; and
- a time delaying means disposed on an optical path of the probe beam and capable of delaying a time at which the amplitude intensity is detected by the detecting means, wherein the pump beam is split into two split pump beams by the first beam splitter; one split pump beam of the two split pump beams is radiated onto the semiconductor corresponding to the detected region; the other split pump beam is radiated onto the semiconductor corresponding to the reference region; pulsed electromagnetic waves generated from the semiconductor corresponding to the detected region and the reference region are focused by the focusing means to be incident on the detecting means provided in singular, wherein the probe beam passes through the time delaying means to be radiated onto the detecting means in synchronization with a timing at which the pulsed electromagnetic waves generated by the respective pump beams are made incident, and wherein the amplitude intensity of each of the pulsed electromagnetic waves that are generated by the respective pump beams and made incident on the detecting means at a timing at which the probe beam is radiated, is detected.

3. The measuring device that uses the pulsed electromagnetic wave according to claim 2, wherein the time delaying means is able to periodically delay the timing at which the amplitude intensity is detected by the detecting means.

4. The measuring device that uses the pulsed electromagnetic wave according to claim 1 further comprising:
- a second beam splitter configured to split the pulsed laser beam into two beams of a probe beam and a pump beam; and
- a pulse timing adjusting means disposed on an optical path of the pump beam between the first beam splitter and the semiconductor and capable of adjusting a pulse timing of the pump beam as desired, wherein the pump beam is split into two split pump beams by the first beam splitter; one split pump beam of the two split pump beams is radiated onto the semiconductor corresponding to the detected region; the other split pump beam is radiated onto the semiconductor corresponding to the reference region; either one of the one split pump beam and the other split pump beam passes through the pulse timing adjusting means; pulsed electromagnetic waves generated from the semiconductor corresponding to the detected region and the reference region are focused by the focusing means to be incident on the detecting means provided in singular, wherein the pulse timing adjusting means is configured to preliminarily adjust the pulse timing of one of the one split pump beam and the other split pump beam so that detection timings of the respective amplitude intensities of the pulsed electromagnetic waves detected by the detecting means match, wherein the probe beam is radiated onto the detecting means in synchronization with a timing at which the pulsed electromagnetic waves generated by the respective pump beams are made incident, and wherein the amplitude intensity of each of the pulsed electromagnetic waves that are generated by the respective pump beams and made incident on the detecting means at a timing at which the probe beam is radiated, is detected.

5. A measuring method that uses a pulsed electromagnetic wave and uses:
- a substance detecting plate including a semiconductor and an insulator formed on the semiconductor;
- a means configured to radiate a pulsed laser beam onto the substance detecting plate from a side of the semiconductor to generate a pulsed electromagnetic wave with an amplitude intensity depending on an amount of a detection object substance at an irradiated position; and
- a detecting means configured to detect the amplitude intensity of the pulsed electromagnetic wave, to measure a change in a state of a solution containing the detection object substance from the amplitude intensity, the measuring method comprising:
- a splitting step of splitting the pulsed laser beam into two beams of a probe beam and a pump beam;
- an incidence step of splitting the pump beam into two split pump beams, radiating one split pump beam of the two split pump beams onto the semiconductor corresponding to a detected region into which a solution containing the detection object substance is able to be introduced, radiating the other split pump beam onto the semiconductor corresponding to a reference region into which a reference solution is able to be introduced, focusing pulsed electromagnetic waves generated from the semiconductor corresponding to the detected region and the reference region so that the pulsed electromagnetic waves are made incident on the detecting means provided in singular;
- a step of radiating the probe beam onto the detecting means in synchronization with a timing at which the pulsed electromagnetic waves generated by the respective pump beams are made incident, the probe beam being subjected to time delay at a predetermined cycle;
- a time-domain waveform generating step of detecting the amplitude intensity of each of the pulsed electromagnetic waves that are generated by the respective pump beams and made incident on the detecting means at a timing at which the probe beam is radiated, thereby acquiring the amplitude intensity of each of a plurality of the pulsed electromagnetic waves respectively in the detected region and the reference region and being different in delay time, and producing a time-domain waveform of the pulsed electromagnetic waves respectively in the detected region and the reference region;

an amplitude acquisition step of acquiring an amplitude intensity at each wave peak position from the time-domain waveform of the pulsed electromagnetic waves produced by the time-domain waveform generating step in each of the detected region and the reference region; and a differentiation step of differentiating the amplitude intensities respectively at the wave peak position in the detected region and the wave peak position in the reference region.

6. A measuring method that uses a pulsed electromagnetic wave and uses:

a substance detecting plate including a semiconductor and an insulator formed on the semiconductor;

a means configured to radiate a pulsed laser beam onto the substance detecting plate from a side of the semiconductor to generate a pulsed electromagnetic wave with an amplitude intensity depending on an amount of a detection object substance at an irradiated position; and a detecting means configured to detect the amplitude intensity of the pulsed electromagnetic wave, to measure a change in a state of a solution containing the detection object substance from the amplitude intensity, the measuring method comprising:

a splitting step of splitting the pulsed laser beam into two beams of a probe beam and a pump beam;

an incidence step of splitting the pump beam into two split pump beams, radiating one split pump beam of the two split pump beams onto the semiconductor corresponding to a detected region into which a solution containing the detection object substance is able to be introduced, radiating the other split pump beam onto the semiconductor corresponding to a reference region into which a reference solution is able to be introduced, focusing pulsed electromagnetic waves generated from the semiconductor corresponding to the detected region and the reference region so that the pulsed electromagnetic waves are made incident on the detecting means provided in singular;

a pulse arrival timing adjusting step of preliminary adjusting a pulse timing of one of the one split pump beam and the other split pump beam such that detection timings of the respective amplitude intensities of the pulsed electromagnetic waves detected by the detecting means match;

a step of radiating the probe beam onto the detecting means in synchronization with a timing at which the pulsed electromagnetic waves generated by the respective pump beams are made incident; and a step of detecting the amplitude intensity of each of the pulsed electromagnetic waves that are generated by the respective pump beams and made incident on the detecting means at a timing at which the probe beam is radiated.

* * * * *